United States Patent
Lock et al.

(10) Patent No.: US 8,070,800 B2
(45) Date of Patent: Dec. 6, 2011

(54) TRANSCATHETER HEART VALVE PROSTHESES

(75) Inventors: James E. Lock, Chestnut Hill, MA (US); Doff B. McElhinney, Milton, MA (US)

(73) Assignee: Children's Medical Center Corporation, Boston, MA (US)

( * ) Notice: Subject to any disclaimer, the term of this patent is extended or adjusted under 35 U.S.C. 154(b) by 316 days.

(21) Appl. No.: 12/299,746

(22) PCT Filed: May 3, 2007

(86) PCT No.: PCT/US2007/010768
§ 371 (c)(1),
(2), (4) Date: Apr. 29, 2009

(87) PCT Pub. No.: WO2007/130537
PCT Pub. Date: Nov. 15, 2007

(65) Prior Publication Data
US 2009/0222082 A1    Sep. 3, 2009

Related U.S. Application Data

(60) Provisional application No. 60/798,418, filed on May 5, 2006.

(51) Int. Cl.
*A61F 2/24* (2006.01)
(52) U.S. Cl. ................................. 623/2.11; 623/2.14
(58) Field of Classification Search ........ 623/1.24–1.26, 623/2.11–2.19, 1.11; 606/108, 191, 194, 606/200
See application file for complete search history.

(56) References Cited

U.S. PATENT DOCUMENTS

| | | | |
|---|---|---|---|
| 3,570,014 A | 3/1971 | Hancock | 3/1 |
| 4,733,665 A | 3/1988 | Palmaz | 128/343 |
| 5,411,552 A | 5/1995 | Andersen et al. | 623/2 |
| 5,840,081 A | 11/1998 | Andersen et al. | 623/2 |
| 5,935,163 A | 8/1999 | Gabbay | 623/2 |
| 5,957,949 A | 9/1999 | Leonhardt et al. | 623/1.24 |
| 6,168,614 B1 | 1/2001 | Andersen et al. | 623/1 |
| 6,174,329 B1 | 1/2001 | Callol et al. | 623/1.34 |
| 6,350,282 B1 | 2/2002 | Eberhardt | 623/2.13 |
| 6,371,983 B1 * | 4/2002 | Lane | 623/2.14 |
| 6,425,916 B1 * | 7/2002 | Garrison et al. | 623/2.11 |
| 6,458,153 B1 | 10/2002 | Bailey et al. | 623/1.24 |
| 6,893,460 B2 * | 5/2005 | Spenser et al. | 623/2.14 |
| 6,908,481 B2 | 6/2005 | Cribier | 623/2.11 |
| 7,198,646 B2 | 4/2007 | Figulla et al. | 623/900 |
| 7,261,732 B2 * | 8/2007 | Justino | 623/1.24 |
| 7,470,285 B2 * | 12/2008 | Nugent et al. | 623/2.18 |
| 7,585,321 B2 * | 9/2009 | Cribier | 623/2.14 |
| 7,758,632 B2 * | 7/2010 | Hojeibane et al. | 623/1.24 |

(Continued)

FOREIGN PATENT DOCUMENTS
WO     98/29057     7/1998
(Continued)

*Primary Examiner* — Kathleen Sonnett
(74) *Attorney, Agent, or Firm* — K&L Gates LLP

(57) ABSTRACT

The present teachings relate to a heart valve prosthesis. The heart valve prosthesis includes a docking station (77) having a wire frame defining a lumen and a valve frame (91) for positioning within its lumen. The docking station includes a diaphragm (78) adapted to have an open position and a closed position, which provides a temporary control mechanism for preventing free regurgitation during the time period between the deployment of the docking station and the deployment of the valve frame, and a sealing mechanism for preventing paravalvar leakage.

19 Claims, 18 Drawing Sheets

U.S. PATENT DOCUMENTS

| | | | |
|---|---|---|---|
| 2002/0032481 A1 | 3/2002 | Gabbay | 623/1.24 |
| 2002/0188348 A1 | 12/2002 | DiMatteo et al. | 623/1.24 |
| 2003/0199963 A1 | 10/2003 | Tower et al. | 623/1.11 |
| 2004/0019374 A1* | 1/2004 | Hojeibane et al. | 623/1.13 |
| 2004/0049262 A1 | 3/2004 | Obermiller et al. | 623/1.15 |
| 2004/0122516 A1 | 6/2004 | Fogarty et al. | 623/2.37 |
| 2004/0186563 A1 | 9/2004 | Lobbi | 623/2.11 |
| 2005/0043790 A1 | 2/2005 | Seguin | 623/2.18 |
| 2005/0137682 A1* | 6/2005 | Justino | 623/1.24 |
| 2005/0234546 A1* | 10/2005 | Nugent et al. | 623/2.11 |
| 2005/0251251 A1* | 11/2005 | Cribier | 623/2.11 |
| 2006/0052867 A1 | 3/2006 | Revuelta et al. | 623/2.18 |

FOREIGN PATENT DOCUMENTS

| | | |
|---|---|---|
| WO | 00/44313 A1 | 8/2000 |
| WO | 03/003943 | 1/2003 |
| WO | 2006/127765 | 11/2006 |
| WO | 2007/081820 A1 | 7/2007 |

* cited by examiner

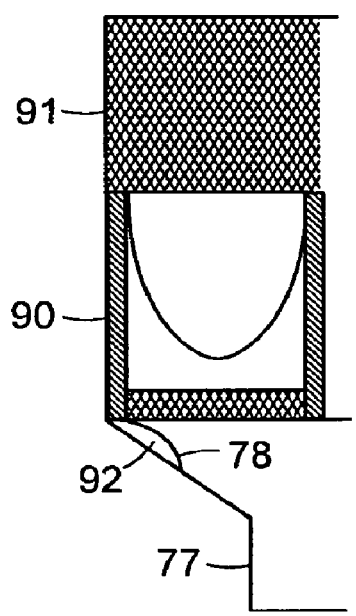
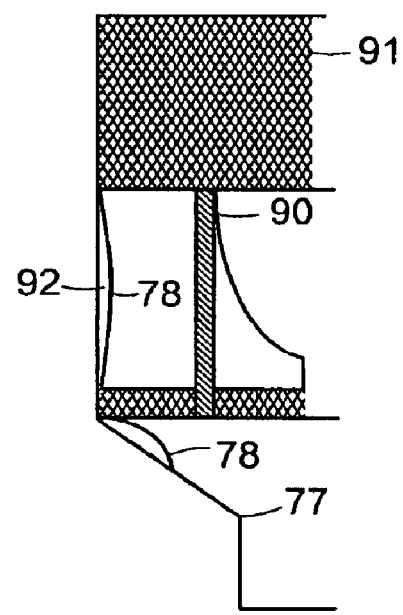
FIG. 19A        FIG. 19B
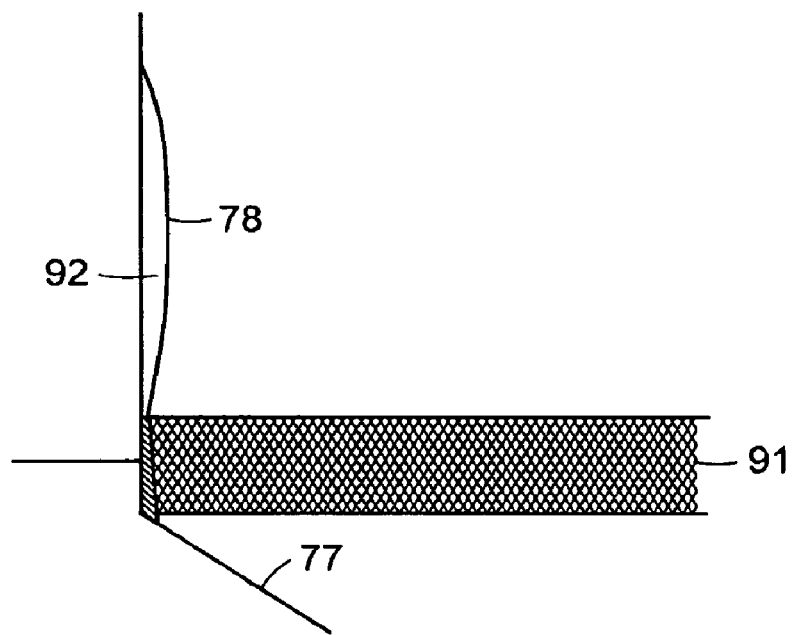
FIG. 19C

TRANSCATHETER HEART VALVE PROSTHESES

CROSS-REFERENCE TO RELATED APPLICATIONS

This application is the national phase of International (PCT) Application No. PCT/US2007/010768, filed on May 3, 2007, which claims the benefit of and priority to U.S. Provisional Patent Application Ser. No. 60/798,418, filed on May 5, 2006. The disclosure of each of the above patent applications is incorporated by reference herein in its entirety.

TECHNICAL FIELD

The present teachings relate generally to the treatment of heart valve dysfunction and, in particular, to minimally invasive systems and methods for replacing such heart valves.

BACKGROUND

There are four valves within the human heart that serve to direct the flow of blood through the two sides of the heart in a forward direction. On the left (systemic) side of the heart are the mitral valve, located between the left atrium and the left ventricle, and the aortic valve, located between the left ventricle and the aorta. These two valves direct oxygenated blood coming from the lungs, through the left side of the heart, into the aorta for distribution to the body. On the right (pulmonary) side of the heart are the tricuspid valve, located between the right atrium and the right ventricle, and the pulmonary valve, located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these heart valves are passive structures that do not expend any energy themselves and do not perform any active contractile function. They consist of moveable leaflets that are designed simply to open and close in response to differential pressures on either side of the valve. The mitral and tricuspid valves are referred to as atrioventricular valves because of their location between an atrium and a ventricle on each side of the heart. The mitral valve has two leaflets and the tricuspid valve has three. The aortic and pulmonary valves are referred to as semilunar valves because of the unique appearance of their leaflets, which are more aptly termed cusps and are shaped somewhat like a half-moon. The aortic and pulmonary valves each have three cusps.

The three cusps are soft tissue structures attached to a wall of the valve in an area designated as the annulus. In the case of the aortic valve, the three cusps are pushed open against the wall of the aorta during systole (when the left ventricle contracts), thereby allowing blood to flow through. During diastole (when the left ventricle relaxes), the left ventricular pressure falls and the aortic valve cusps reapproximate (the three cusps fall away from the wall and close), thereby preventing the blood which has entered the aorta from regurgitating (leaking) back into the left ventricle.

Heart valves may exhibit abnormal anatomy and function as a result of congenital or acquired valve disease. Problems with heart valve functions can be classified into two categories: 1) stenosis, in which a valve does not open properly, or 2) insufficiency (also called regurgitation), in which a valve does not close properly. Due to the higher-pressure gradient, the mitral and aortic valves are subject to greater fatigue and/or risk of disease. Also, while mitral valves often can be surgically repaired, most abnormalities of the aortic valve require replacement.

Prosthetic heart valves used to replace diseased or abnormal natural heart valves include mechanical devices with, for example, a rigid orifice ring and rigid hinged leaflets or ball-and-cage assemblies, and bioprosthetic devices that combine a mechanical assembly with biological material (e.g., human, porcine, bovine, or biopolymer leaflets).

In the past, heart valve replacement typically required median sternotomy and cardiopulmonary bypass. More recently, various prosthetic heart valves that can be implanted by less invasive procedures have been developed. For example, various replacement heart valve apparatus that can be delivered via an endovascular transcatheter approach are described in co-owned, co-pending U.S. patent application Ser. Nos. 11/052,466 and 60/757,813, the entire disclosures of which are incorporated by reference herein for all purposes. The replacement heart valve apparatus described in these patent applications generally include a compressible valve frame and a compressible docking station that is deployed prior to the introduction of the valve frame into a patient's heart. The valve frame is subsequently positioned within the docking station, which helps to support and anchor the valve frame in the desired location.

Like other transcatheter heart valves that are currently known or available, implantation of the aforementioned replacement heart valve apparatus in the aortic position (as opposed to the pulmonic position) presents unique challenges due to its close proximity to both the mitral valve and the coronary ostia, as well as high systemic pressures and the inability of the body to tolerate free leakage through the aortic valve for any period of time. For example, the implantation of the docking station in the aortic position can require coverage and complete immobilization of the native aortic valve, which will cause free regurgitation. Similar difficulties and challenges, albeit to a slighter extent, can be expected with implanting the replacement heart valve apparatus in other positions, for example, the mitral position, in which case, free regurgitation into the lungs via the left atrium can occur. Acute free regurgitation, even for the short period of time necessary to deliver the valve component within the docking station, is unlikely to be tolerated by the patient, particularly in the target population of patients with pre-existing heart conditions due to stenosis and/or regurgitation. While theoretically, a patient can be put on cardiopulmonary bypass to prevent or reduce such regurgitation, the various health risks associated with a bypass procedure make this an impractical option for many patients in the target population.

The present teachings, therefore, relate to an improved transcatheter heart valve prosthesis adapted to be implanted in the aortic position. However, the present teachings can be adapted for the replacement of other anatomical valves.

SUMMARY

The present teachings solve the above-identified problem by providing transcatheter heart valve prostheses that can be delivered to and anchored in a patient's heart to replace or assist the function of a native heart valve. However, it should be understood that the present teachings also are applicable to replace a replacement heart valve, e.g., one that has ceased functioning optimally. The present teachings also relate to methods of making and using the heart valve prostheses.

In one aspect, the present teachings relate to a heart valve prosthesis including a docking station that includes a wire frame defining a lumen and a replacement heart valve that includes a valve frame for positioning within the lumen of the docking station. The heart valve prosthesis also includes a diaphragm attached to the wire frame of the docking station and positioned within the lumen of the docking station. The diaphragm can be adapted to have an open position and a close position. The present teachings also recognize the docking station and the diaphragm as an independent and useful medical device. More specifically, the present teachings provide a medical device comprising a docking station comprising a wire frame defining a lumen, and a diaphragm positioned within the lumen and attached to the wire frame of the docking station, and can be adapted to have an open position and a closed position. It should be understood that the teachings herein in connection with the docking station and diaphragm of a heart valve prostheses apply equally to the medical device comprising a docking station and a diaphragm.

The docking station can define a generally cylindrical body that has a wall defining a lumen. The wall can include an outer surface (in contact with heart tissues when implanted) and an inner surface (in contact with blood flow when implanted), and the thickness of the wall can be constant throughout the length of the docking station or can be unevenly distributed between the outer surface and the inner surface. The docking station as a whole can include one or more portions with a substantially constant diameter (e.g., a cylindrical portion) and/or one or more portions with a varying diameter (e.g., a bulbous portion or a concave portion).

In some embodiments, the docking station can have an expanded position and a compressed position. The ability of the docking station to be compressed radially allows transcatheter delivery of the heart valve prosthesis. The docking station can be self-expandable or balloon-expandable. Depending on its intended implantation site, the docking station can include one or more openings such that its implantation does not obstruct anatomical openings, for example, the coronary ostia. The docking station also can include radiopaque markers to allow visualization of the positioning of the docking station during its delivery and deployment. Visualization techniques such as fluoroscopy can be used. The radiopaque markers also can facilitate a medical practitioner to more precisely determine the diamater of the deployed docking station, which allows optimal sizing of the replacement heart valve.

The diaphragm attached to the docking station can help to prevent or reduce free regurgitation when the docking station is deployed at or near a native heart valve in a way that covers and/or immobilizes the native heart valve. The diaphragm can serve as a temporary control mechanism of blood flow prior to the introduction and deployment of the more permanent replacement heart valve. The diaphragm can open and close in response to differential pressures on either of its sides similar to the native heart valve and the replacement heart valve. In some embodiments, the diaphragm can function as a barrier that absorbs and/or restricts blood flow. Subsequent to the deployment of the replacement heart valve, the diaphragm can continue to function as a sealing mechanism that prevents paravalvar leakage.

In some embodiments, the diaphragm can be a unitary piece of material such as a membrane made of biological or synthetic materials. The membrane can include one or more slits that divide the membrane into multiple connected sections. In some embodiments, the diaphragm can include a plurality of leaflets. These leaflets can extend circumferentially along the diaphragm in an overlapping or non-overlapping configuration.

In some embodiments, the diaphragm can be directly attached to the wall of the docking station by sutures, adhesives, or other methods known in the art. In other embodiments, the diaphragm can be indirectly attached to the wall of the docking station, such as to a piece of material (e.g., a membrane) that itself is directly attached to the wall of the docking station. The diaphragm can be attached to any portion of the docking station within its lumen.

The valve frame of the replacement heart valve can include a substantially cylindrical body defining a lumen and a plurality of valve members attached to the substantially cylindrical body. In some embodiments, each of the valve members can include one or more curved wires and a leaflet. In certain embodiments, each of the valve members can include an inner curved wire support structure and an outer curved wire support structure. The leaflet of the valve member can include a leaflet body and one or more leaflet projections. In some embodiments, the one or more projections can be attached to a respective inner curved support structure and the leaflet body can extend over a respective outer curved support structure so as to position the leaflet body within the lumen of the valve frame of the replacement heart valve.

Another aspect of the present teachings relate to a method of delivering a heart valve prosthesis to an anatomical site. The method can include introducing a heart valve prosthesis of the present teachings into the heart through a catheter, deploying the docking station, and introducing a replacement heart valve into the lumen of the docking station through a catheter, and deploying the replacement heart valve within the lumen of the docking station so that the leaflets of the diaphragm are pressed between the wire frame of the docking station and the valve members of the replacement heart valve. The method can further include determining a diameter of the deployed docking station using fluoroscopy and choosing a replacement heart valve having a diameter that approximates the diameter of the deployed docking station.

These and other objects, along with the features of the present teachings herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the present teachings.

FIGS. 19A-C illustrate how a diaphragm according to the present teachings can seal potential space between the docking station and the replacement heart valve, thereby preventing paravalvar leakage.

DETAILED DESCRIPTION

Figure 1A:
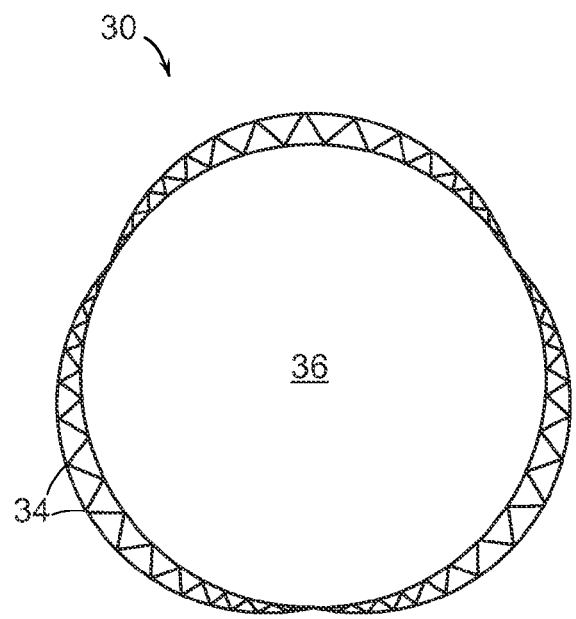
FIGS. 1A and 1B illustrate an embodiment of an expanded docking station according to the present teachings.

The present teachings relate to a heart valve prosthesis that mitigates the potential complications of free regurgitation that may occur during the implantation of a replacement heart valve. Specifically, the present teachings relate to a modification of an existing replacement heart valve apparatus that includes a supporting structure and a replacement heart valve. The supporting structure, such as a docking station, a stent or a scaffold, is adapted to be deployed at a preselected position within an anatomical lumen of the heart via an introducing catheter. The phrase "docking station" is herein used to broadly refer to all types of supporting structures including stents. The replacement heart valve is then inserted into the deployed docking station using the same catheter or, alternatively, a second catheter, and deployed within the lumen of the docking station. A person skilled in the art will recognize that while many features of the replacement heart valve apparatus of the present teachings are adapted for transcatheter delivery, the replacement heart valve apparatus can be implanted via other methods, for example, via various surgical techniques including those in which the delivery catheter and/or the replacement heart valve apparatus can be implanted through a direct incision in or a puncture of, for example, the left ventricle (e.g., for implanting a replacement aortic valve or a replacement mitral valve) or the aorta (e.g., for implanting a replacement aortic valve). Accordingly, embodiments related to transcatheter delivery described herein are to be considered as only illustrative and not restrictive.

While the two-component replacement heart valve apparatus of the present teachings enables the use of smaller catheters because the inner diameter of the catheter need not accommodate, at the same point in time of the procedure, the compressed volume of both a docking station and a valve assembly, the two-part deployment procedure introduces a certain lag time between the deployment of the docking station and the valve assembly. The lag time can be problematic when the docking station needs to be deployed in the same luminal space as the native heart valve. Specifically, the native valve will be forced open by the deployed docking station, which leads to a period of free regurgitation until the introduction and deployment of the valve assembly. Such acute free regurgitation can lead to various clinical complications that are unlikely to be tolerated by patients requiring a heart valve replacement.

To prevent regurgitation, the present teachings provide a modified heart valve prosthesis in which the docking station is provided with a diaphragm. The diaphragm has an open position and a close position similar to the native heart valve and the replacement heart valve in that it can open and close in response to differential pressures on either of its sides. For example, in embodiments where the replacement heart valve prosthesis is placed in the aortic position, blood can still flow out of the left ventricle during ventricular systole, but free regurgitation is prevented, or at least reduced, during diastole because of the presence of this temporary barrier. Similarly, in embodiments where the replacement heart valve prosthesis is placed in the mitral position, the diaphragm can open to allow blood flow during ventricular diastole and atrial systole, but back flow is prevented or reduced during ventricular systole. The patient's heart, therefore, is afforded a stabilizing period before the more permanent replacement heart valve is implanted. Different embodiments of the docking station, the diaphragm, and the replacement heart valve will be described in more detail hereinbelow.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

The docking station of the heart valve prosthesis according to the present teachings can be a self-expandable or a balloon-expandable stent that can be compressed radially to a desirable French size. In some embodiments, the docking station can be dimensioned to fit in a catheter having a diameter no larger than about 22 Fr (7.3 mm). For example, the docking station can have a diameter of about 5 mm or less when crimped. When expanded, the widest portion of the docking station can have a diameter of about 30 mm, and the narrowest portion can have a diameter of about 25 mm.

Figure 1B:
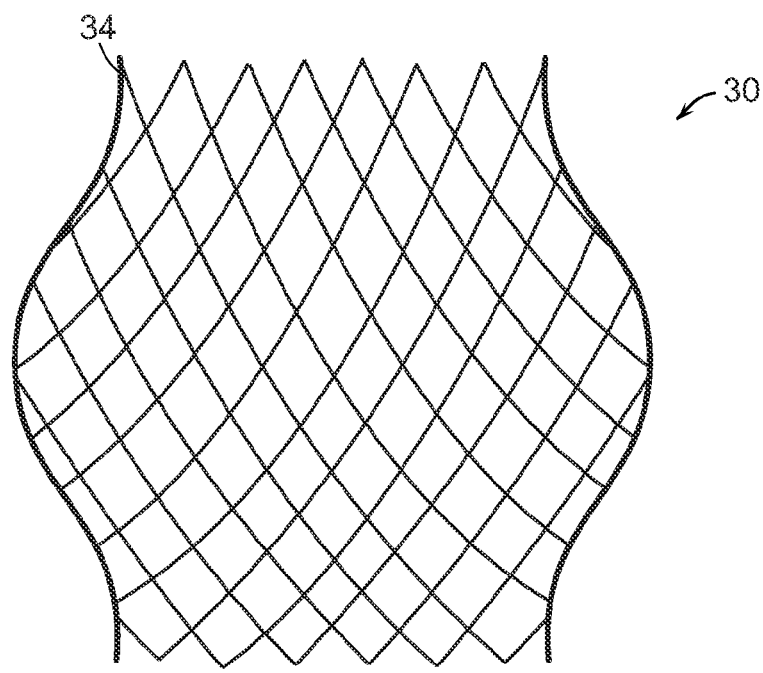

As shown in FIGS. 1A and 1B, one embodiment of a docking station 30 according to the present teachings can define a generally cylindrical body that has a wall 34 defining a lumen 36. The wall can include an outer surface (in contact with heart tissues when implanted) and an inner surface (in contact with blood flow when implanted), and the thickness of the wall can be constant throughout the length of the docking station or can be unevenly distributed between the outer surface and the inner surface. The docking station 30, both longitudinally and in terms of its cross-section, can define various shapes and can be made to approximate or be compatible with the anatomical site where it is intended to be implanted. For example, in some embodiments, the cross-section of the docking station can be circular, elliptical, or define other eccentric shapes. In some embodiments, the docking station as a whole can be, without limitation, generally, substantially, or somewhat cylindrical, conical, spherical, barrel-like, or hourglass-like. By way of illustration, for a docking station adapted to be implanted in the aortic position, its general shape can be tubular with a relatively long major axis (i.e., parallel to the direction of blood flow), while a docking station adapted to be implanted in the mitral position can be concave in shape and relatively short in its major axis to accommodate the geometry of the mitral annulus and to avoid interference with the blood flow into the left ventricle.

To further illustrate, the geometry of the docking station can resemble, without limitation, one of the four embodiments illustrated in FIGS. 2A-D.

Figure 2A:
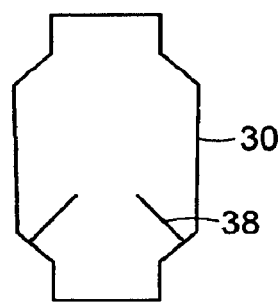
FIGS. 2A-2D illustrate certain embodiments of an expanded docking station along with a diaphragm attached within its lumen according to the present teachings.

Referring to FIG. 2A, in some embodiments, the docking station can include a first cylindrical portion at one end and a second cylindrical portion at the other end, and an intermediate portion therebetween, where the intermediate portion also can be cylindrical but have a larger diameter than the first cylindrical portion and the second cylindrical portion. There also can be a tapered portion extending from each of the first cylindrical portion and the second cylindrical portion to the intermediate portion as shown in FIG. 2A.

Figure 2B:
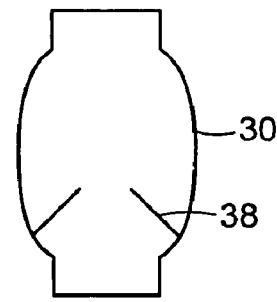

FIG. 2B shows another embodiment of a docking station. The docking station can have a first cylindrical portion and a second cylindrical portion similar to the embodiment shown in FIG. 2A. The intermediate portion, however, can be of a bulbous or barrel shape that again has a greater diameter than the first and second cylindrical portions.

Figure 2C:
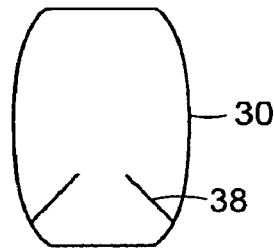
Figure 2D:
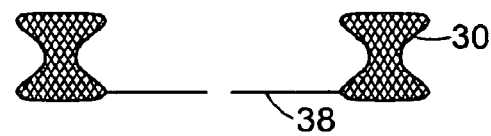

Other embodiments of the docking station are illustrated in FIGS. 2C and 2D. Referring to FIG. 2D, the docking station can have a relatively short major axis and a relatively wide diameter. And unlike FIGS. 1B, 2A and 2B all of which show a docking station with a wider intermediate portion, the docking station can include terminal portions that are wider than the intermediate portion, for example, similar to the shape of an hourglass, as shown in FIG. 2D. Also, the wall of the docking station can have varying thickness as shown in FIG. 2D. For example, the wider terminal portions can be a thicker wall compared to the narrower intermediate portion. A docking station having a shape that resembles the docking station shown in FIG. 2D can be well-adapted for placement in the mitral position. Its external contour, for example, can conform to the space between the left ventricle and the left atrium, while its internal contour can allow the stable positioning of the valve frame to be placed therein. In some embodiments, the terminal portions (e.g., the first cylindrical portion and the second cylindrical portion in FIGS. 2A and 2B) of the docking station can have the same or a different diameter, and can be absent in some embodiments as shown in FIG. 2C.

In some embodiments, the docking station can be made of a slotted tube or a series of interconnected wires that together form an expandable mesh or wire frame. In addition to the interstices of the mesh, the wire frame can include additional larger openings that represent openings native to the implantation site. For example, if the implantation site is at or near the aortic valve, the docking station can include one or more openings to allow fluid communication with the coronary ostia.

The docking station can be made of various materials that are compatible with placement in the body, that possess desirable material wear properties and/or that have a minimal risk of causing infection in the body of the patient. Examples of suitable materials include shape memory materials, stainless steel alloys, molybdenum alloys, pyrolitic carbon, and certain polymers. For example, the wire frame can be constructed from strips of a shape memory material. By way of example, the shape memory material can be nickel-titanium wire sold under the product name nitinol. The nickel-titanium wire, when properly manufactured, exhibits elastic properties that allow the wire to be manipulated (e.g., bent) by an operator and then returned to, substantially, the same shape the wire possessed prior to it being manipulated. The wire can return to substantially its original shape when the operator heats the wire or, alternatively, when the operator removes the forces applied to bend the wire.

Other than the French size advantage mentioned above, the two-component replacement heart valve apparatus also affords the additional benefit of allowing optimal sizing of the replacement heart valve to be implanted. After deployment, the docking station, whether self-expandable or balloon-expandable, can have a final diameter that is slightly different than what is originally anticipated, as tissue compliance cannot always be accurately predicted. When the docking station and the replacement heart valve are delivered in a one-step procedure, the replacement heart valve may turn out to be too big or too small. When the replacement heart valve is too big, leaflet redundancy results, which in turn can lead to premature degeneration of the leaflets. When the replacement heart valve is too small, it may not properly anchor within the docking station and can become embolic. A two-component system provides the medical practitioner an opportunity to determine the final diameter of the deployed docking station and select a replacement heart valve of an optimal dimension. Accordingly, in some embodiments, the docking station can include one or more radiopaque markers or other visualization means to allow visual determination of its deployed dimension.

Figure 3A:
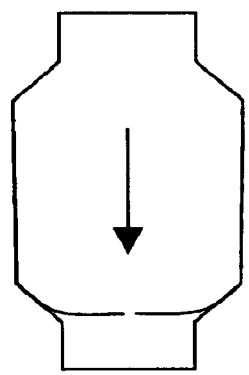
FIGS. 3A-3C illustrate the operation of various embodiments of a diaphragm and possible attachment configurations of such diaphragm within the lumen of a docking station according to the present teachings.
Figure 3B:
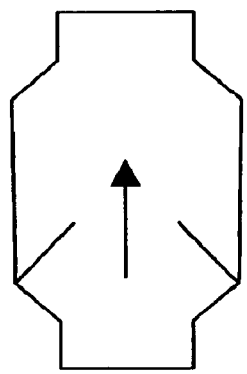
Figure 3C:
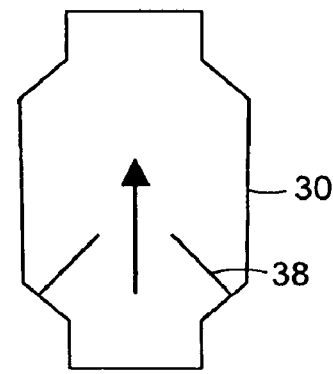

To allow the docking station to be implanted in the same luminal space as the native valve and to prevent free regurgitation, the docking station can include a diaphragm. Referring to FIGS. 3A-C, the diaphragm 38 is adapted to open and close in response to differential pressures on either of its sides. FIG. 3A shows an implanted docking station in which the diaphragm 38 is in the close position and provides a barrier to the back flow of blood (in the direction of the arrow). FIGS. 3B and 3C show an implanted docking station in which the diaphragm 38 is in the open position, allowing blood to flow through the docking station.

The diaphragm can be attached to the docking station by various means, for example, by suturing, adhesives, welding, crimping, insert molding, and the like. The diaphragm can be attached at various positions within the lumen of the docking station. For example, and as shown in FIGS. 3B and 3C, the diaphragm 38 can be attached within the intermediate portion of the docking station, within the tapered portion of the docking station, or within one of the terminal portions of the docking station (not shown). By way of further example, and for application in the aortic position, the diaphragm can be attached just below the openings (provided for the coronary ostia) of the docking station.

Figure 4A:
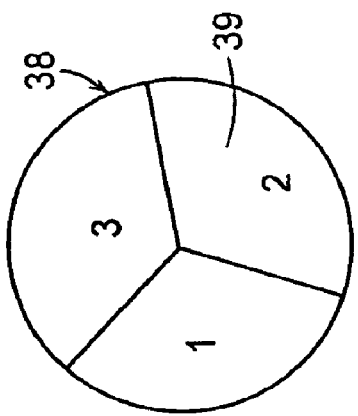
FIGS. 4A-4I illustrate nine different embodiments of a diaphragm according to the present teachings.
Figure 4D:
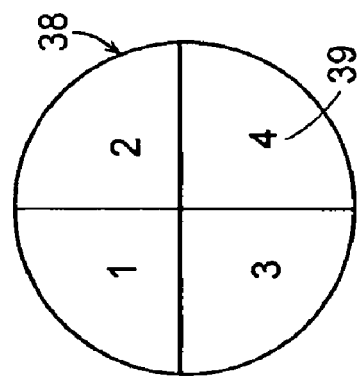
Figure 4B:
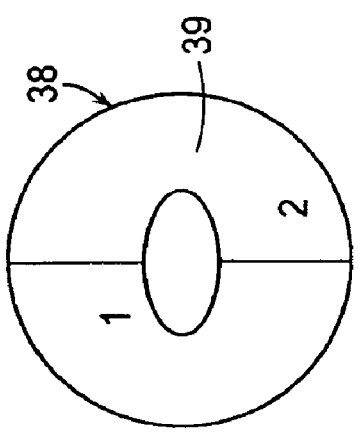
Figure 4E:
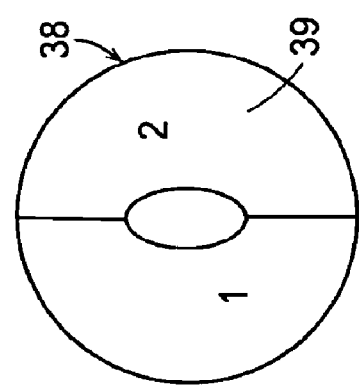
Figure 4C:
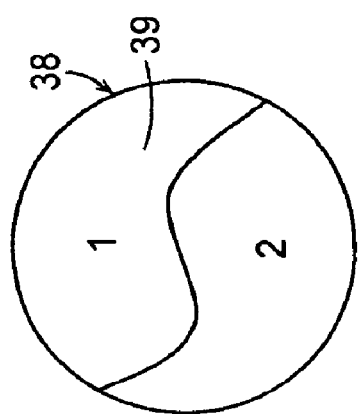
Figure 4F:
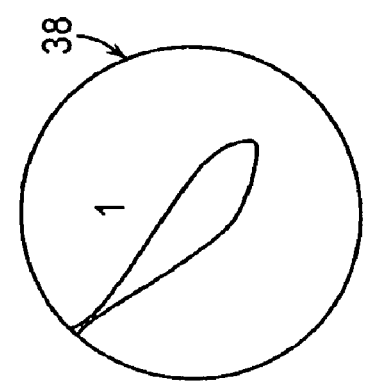
Figure 4I:
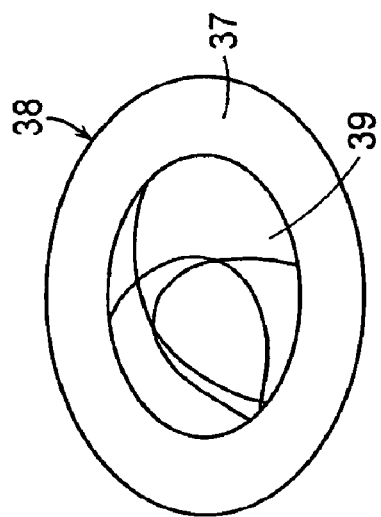
Figure 4H:
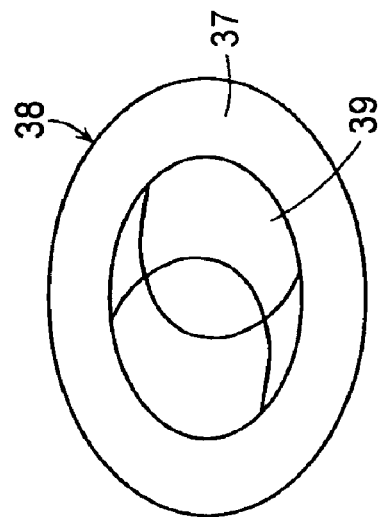
Figure 4G:
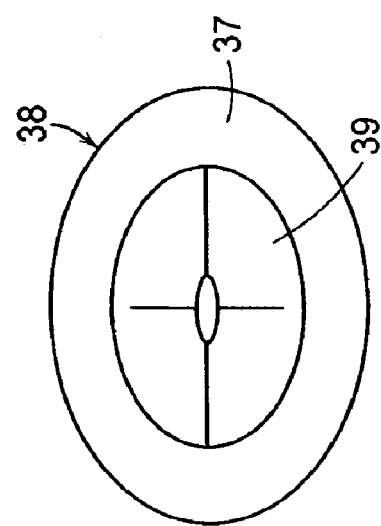

Referring to FIGS. 4A-4I, the diaphragm 38 can be a unitary piece of material or can include a plurality of leaflets 39. With continued reference to FIGS. 4A-4I, the diaphragm 38 can optionally include one or more slits (FIGS. 4A, 4C, 4F and 4G) and/or perforations (FIGS. 4B, 4D, 4E and 4G). For example, and referring to FIG. 4F, the membrane 38 can include two perpendicular slits, giving rise to four sections or leaflets 39. The slits can converge at the center of the diaphragm or at some other point on the diaphragm, and provide an opening for blood to flow through. The diaphragm can have one or more perforations in place of or in addition to the slit(s). The diaphragm can also include an outer reinforcement ring 37 (FIGS. 4G-4I) that can help secure the diaphragm to the docking station and provide enhanced structural integrity to the diaphragm. In some embodiments, the diaphragm can include a plurality of leaflets. The leaflets can extend circumferentially and can be overlapping or non-overlapping. For example, as shown in FIGS. 4A-4C and 4E-4I, the diaphragm can include two, three, four, five or more leaflets. Referring to FIGS. 4B and 4C, the leaflets can have a substantially triangular shape, the tips of which can converge at the concentric point of the diaphragm. In some embodiments and referring to FIGS. 4H and 4I, the leaflets can be substantially semicircular, and can be of the same size or different sizes. As shown in FIGS. 4B, 4D and 4E, the diaphragm can include a perforation or opening in the center of the diaphragm, off-center (not shown), or extending partially along its diameter. In other embodiments (not shown), the leaflets of the diaphragm can be in a curved or spiral-like overlapping configuration, resembling an iris diaphragm found in a camera. Other designs and configurations are within the scope of the present teachings.

The diaphragm can be made of various biocompatible materials. The diaphragm can be made of a biological membrane (e.g., human, ovine, porcine, bovine valve leaflets, pericardium, intestinal lining, or covering tissue, etc.), a bio-engineered material, or a synthetic material (e.g., polymers such as polyethylene, PTFE). In some embodiments, the biological or synthetic material or membrane can be supported by wires made of, for example, nitinol. The diaphragm also can be a wire mesh including flexible metallic struts made of nitinol or other metals or alloys.

Because the diaphragm is designed to function for a limited period of time (the time between the deployment of the docking station and the deployment of the valve assembly can be as short as less than a minute to as long as a few days), the mechanical requirements of the diaphragm are much less demanding than a typical replacement heart valve. For example, the materials used to make the diaphragm can be thinner and have less structural integrity than a more permanent replacement heart valve, which helps to retain the French size advantage of the original two-component replacement heart valve system. In certain embodiments, the diaphragm, in addition to or instead of providing an open and close position, can act as a barrier that can help control the extent of regurgitation by absorbing a certain amount of blood or slowing down blood flow. In these embodiments, the diaphragm can be made of an absorbing material such as various polymeric foams.

Figure 5A:
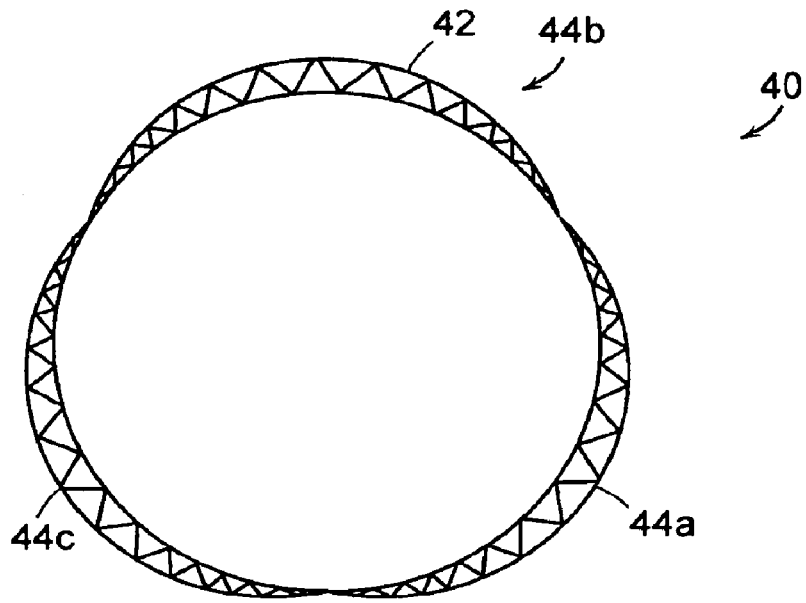
FIGS. 5A-5B show a top-view and a side view of an embodiment of a valve frame according to the present teachings.
Figure 5B:
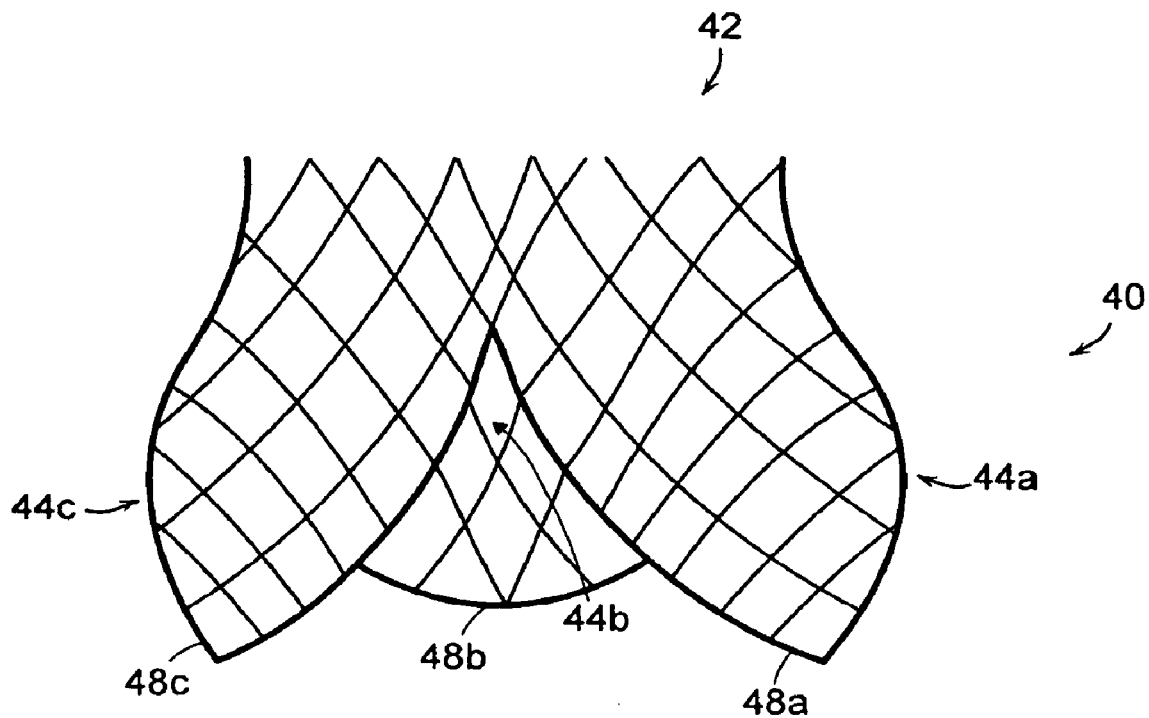

Replacement heart valves that can be used in connection with the aforedescribed docking station and diaphragm include various transcathether replacement heart valves known in the art. For example, and referring to FIGS. 5A and 5B, the replacement heart valve can include a valve frame 40 made of a shape memory material. The valve frame 40 can define a generally cylindrical body that is constructed from a mesh 42. The mesh 42 can be constructed from wires or strips of a shape memory material. The valve frame 40 also can have three valve members 44a, 44b and 44c. The valve members 44a, 44b and 44c can have a free end 48a, 48b and 48c, respectively. The valve frame 40 could, alternatively, be any geometric shape (e.g., cylindrical, conical, spherical or barrel-like) that is compatible with the placement of the valve frame 40 within a docking station, such as the docking station 30 of FIG. 1B.

Figure 6A:
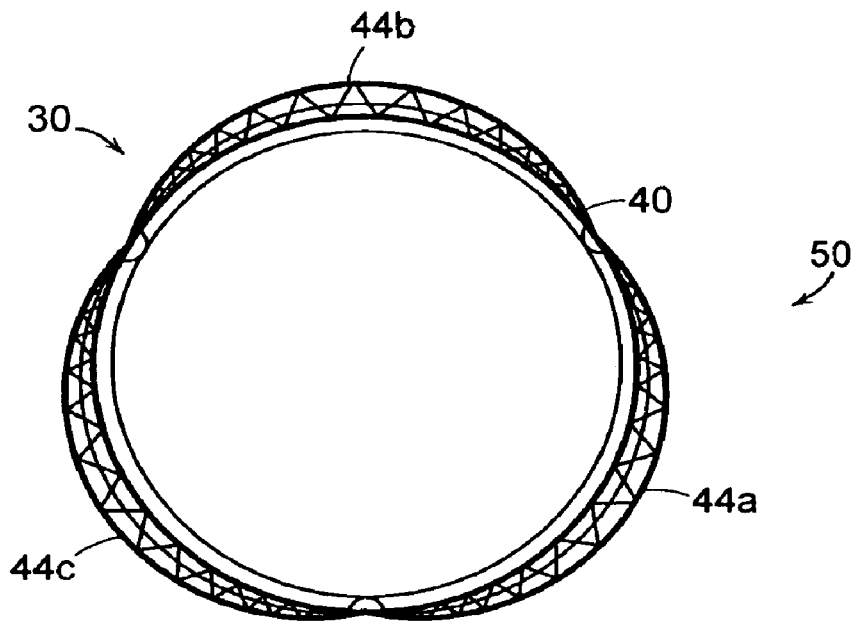
FIGS. 6A and 6B are a top-view and a side-view of the valve frame of FIG. 5A located within the lumen of the docking station of FIG. 1A.
Figure 6B:
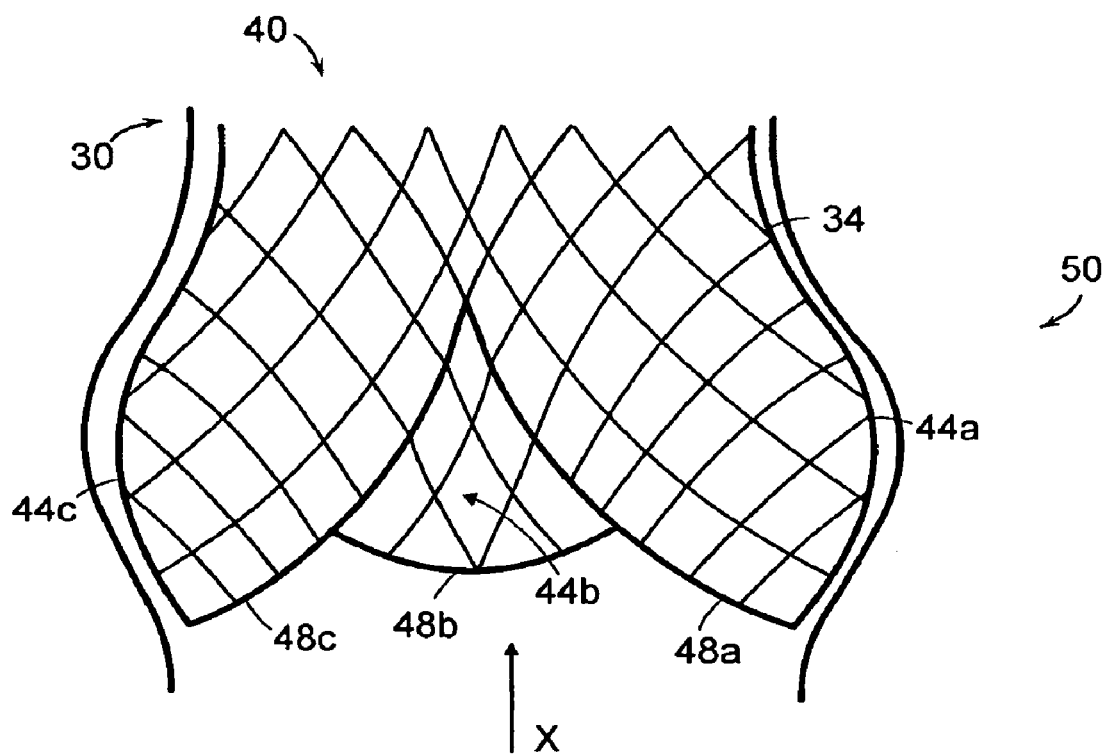

As shown in FIGS. 6A and 6B, the valve frame 40 can be deployed within the lumen 36 of the docking station 30. The valve frame 40 and the docking station 30 are hereinbelow referred to as the valve assembly 50 collectively. The valve frame 40 can be manufactured to ensure that the valve frame 40 can maintain a desired (e.g., fixed) placement with respect to the docking station 30 when the valve frame 40 and the docking station 30 are located within the heart of a patient and subjected to the flow of blood through the valve assembly 50.

Figure 6C:
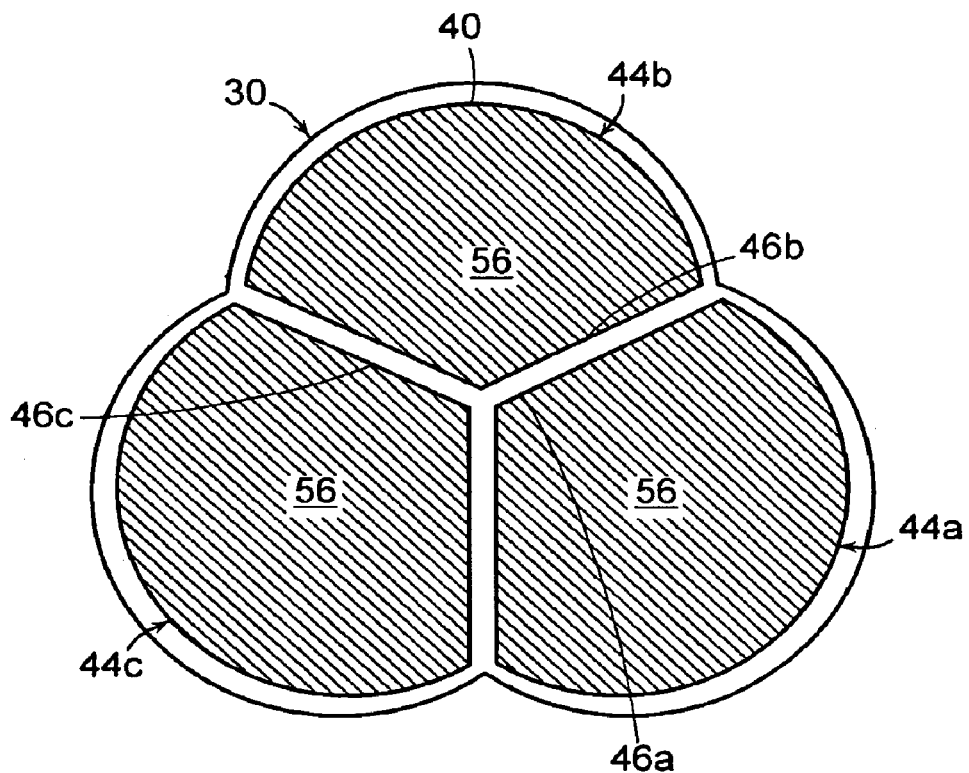
FIGS. 6C and 6D are a top-view and a cross-sectional view of the valve frame and docking station of FIGS. 6A and 6B with the members of the valve frame covered with a cover material and free ends of the cover material located away from the wall of the docking station.
Figure 6D:
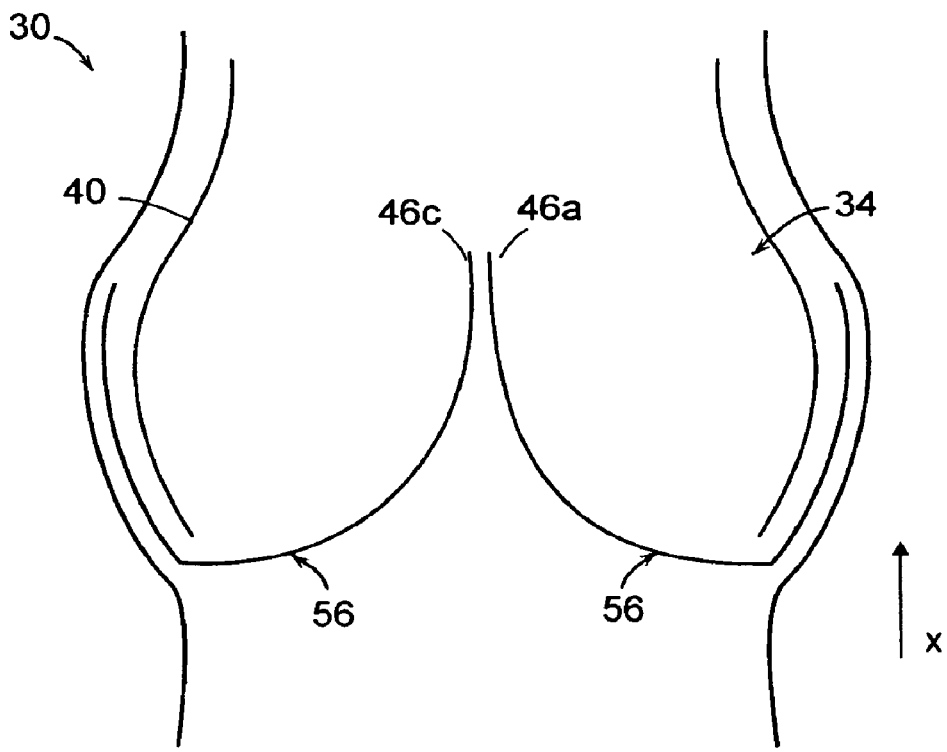

Referring now to FIGS. 6C and 6D, the valve members 44a, 44b and 44c can be coated, typically, with a cover material 56 (e.g., a biocompatible material, such as, silicon rubber or bovine, porcine or human tissue that is chemically treated to minimize the likelihood of rejection by the patient's immune system). The coated valve members can be capable of functioning similarly to the three cusps of the aortic valve, for example. The cover material can be a bio-engineered material that is capable of being applied to the valve members. The cover material can be applied to the valve frame prior to deployment of the valve frame into the body. Again referring to FIGS. 6C and 6D, the cover material 56 can have three free ends 46a, 46b and 46c corresponding to valve members 44a, 44b and 44c, respectively. The free ends also are herein referred to as leaflets.

Figure 6E:
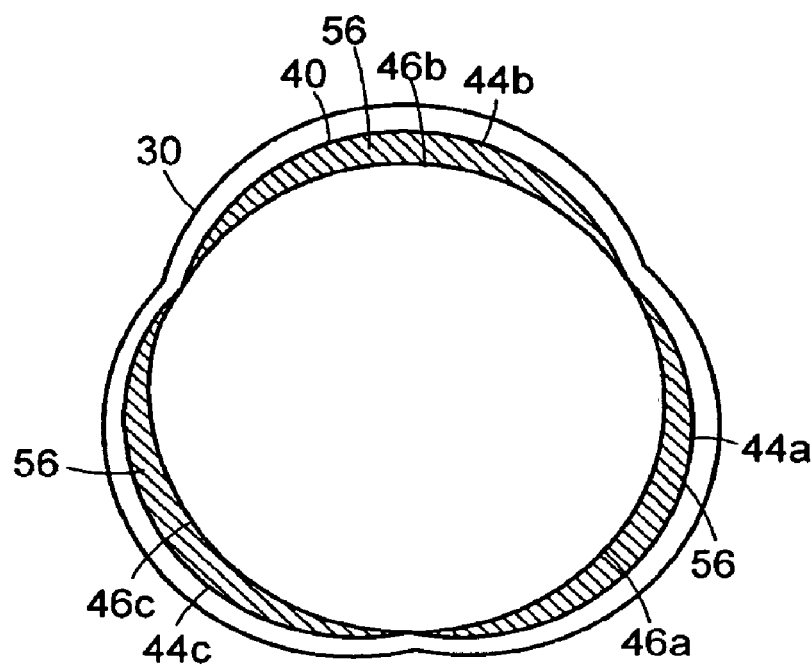
FIGS. 6E and 6F are a top-view and a cross-sectional view of the valve frame and docking station of FIGS. 6C and 6D with the free ends of the cover material located towards the wall of the docking station.
Figure 6F:
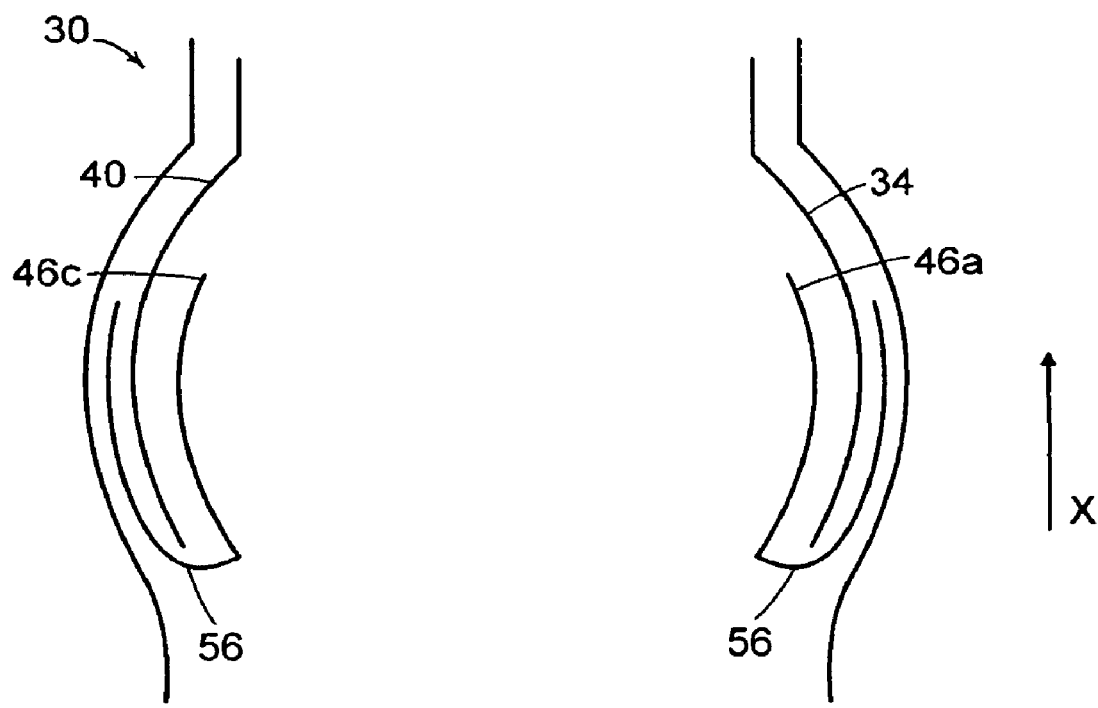

With continued reference to FIGS. 6C and 6D, after placement of the valve frame within the docking station (located within the body), the cover material 56 applied to the valve members 44a, 44b and 44c is capable of, generally, obstructing the flow of blood in the negative direction along the X-axis. The free ends 46a, 46b and 46c move away from the inner wall 34 of the docking station 30, thereby limiting the flow of blood in the negative direction along the X-axis. However, referring now to FIGS. 6E and 6F, as blood flows in the positive direction along the X-axis, the free ends 46a, 46b and 46c of the cover material 56 move towards the inner wall 34 of the docking station 30. The free ends 46a, 46b and 46c, thereby permit the flow of blood through the valve assembly 50. In this manner, the valve assembly approximates the functioning of a natural heart valve of the body by allowing blood to flow in the positive direction along the X-axis.

Figure 7:
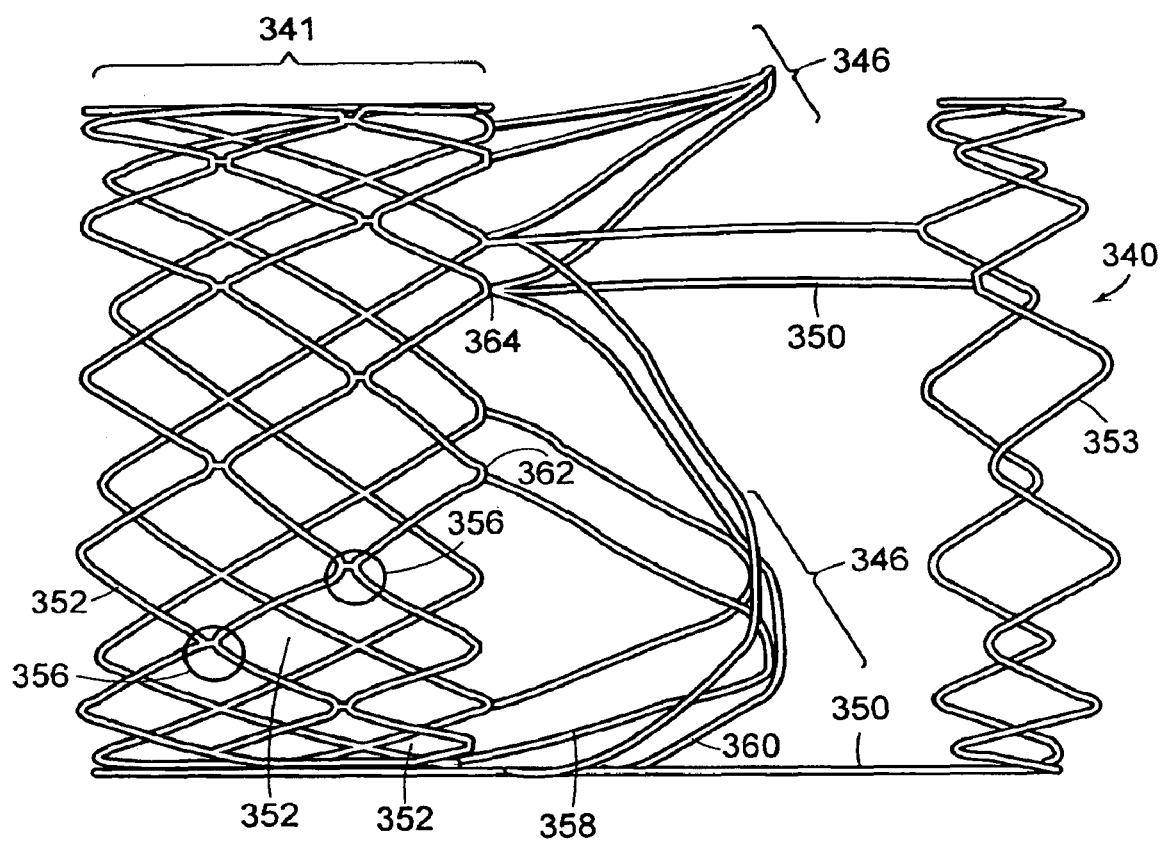
FIG. 7 is a side view of an embodiment of a docking station and a valve frame (without leaflets) according to the present teachings.
Figure 12:
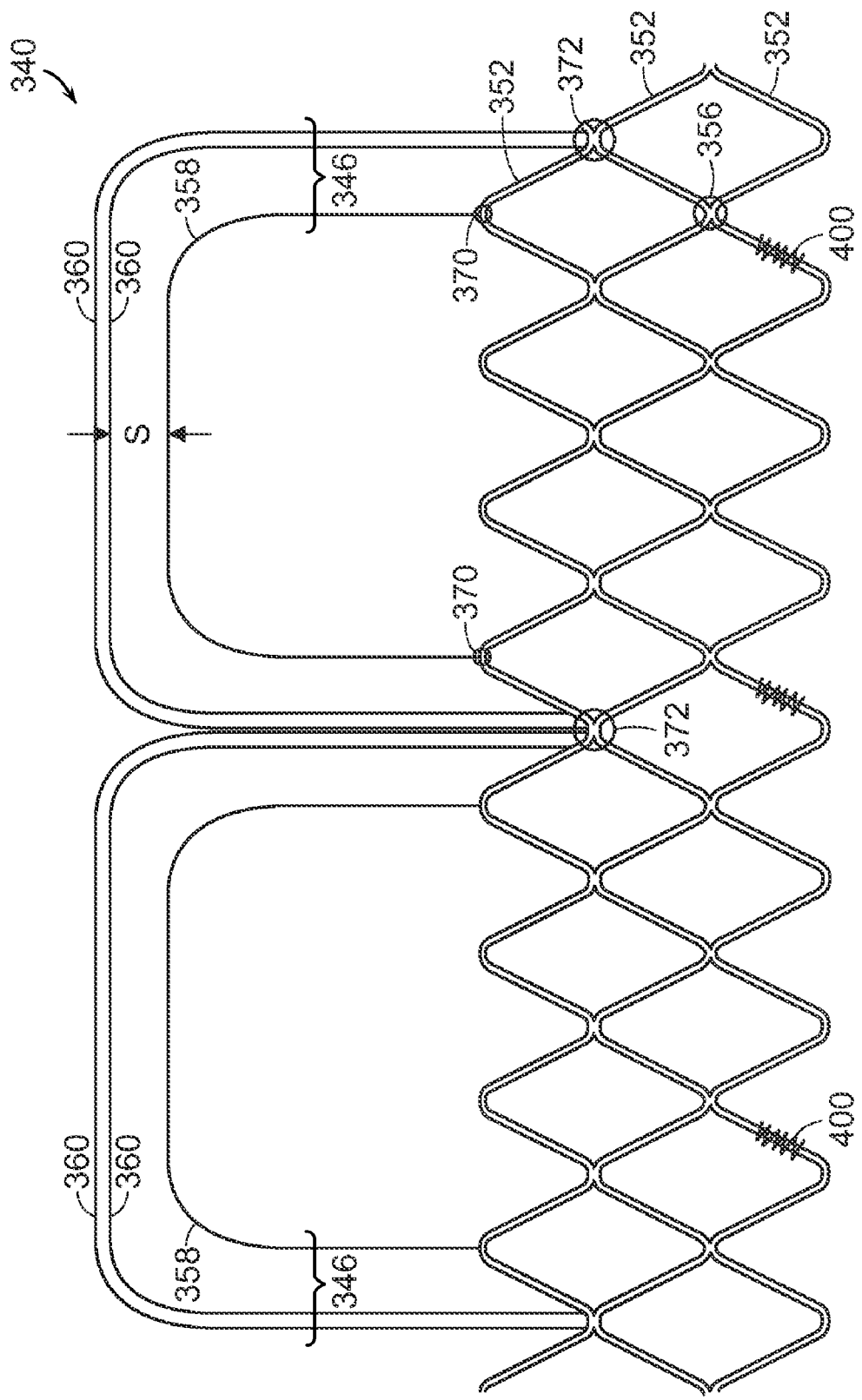
FIG. 12 is an opened view of a portion of yet another embodiment of a valve frame (without leaflets) according to the present teachings.

FIG. 7 shows another embodiment of a valve frame that can be used with the docking station and diaphragm described above. The valve frame 340 includes a substantially cylindrical body portion 341, a plurality of valve attachment pairs 346, and a plurality of standoffs 350 attached to one or more exterior serpentine wire rings 353. In some embodiments, and as shown in FIG. 12, the plurality of standoffs 350 and the one or more exterior serpentine wire rings 353 are absent.

As shown, the substantially cylindrical body portion 341 of the valve frame 340 can be constructed of a plurality of serpentine curved wires 352. Each of the vertices 356 of the serpentine curves of a first wire 352 can be attached at the vertices 356 to each of the vertices of the serpentine curves of an adjacent wire 352. In one embodiment, the wires can be constructed of nitinol. Again the substantially cylindrical body portion 341 can be expandable between a first compressed state (not shown) and a second expanded state (shown). It should be noted that when the terms "vertex" or "trough" are used, the convention is that the term "trough" is a bend in the wire that points in the direction of blood flow (i.e., in the positive direction of X shown in FIG. 8) and a "vertex" is a bend that points in a direction opposite blood flow (i.e., in the negative direction of X shown in FIG. 8.

Figure 8:
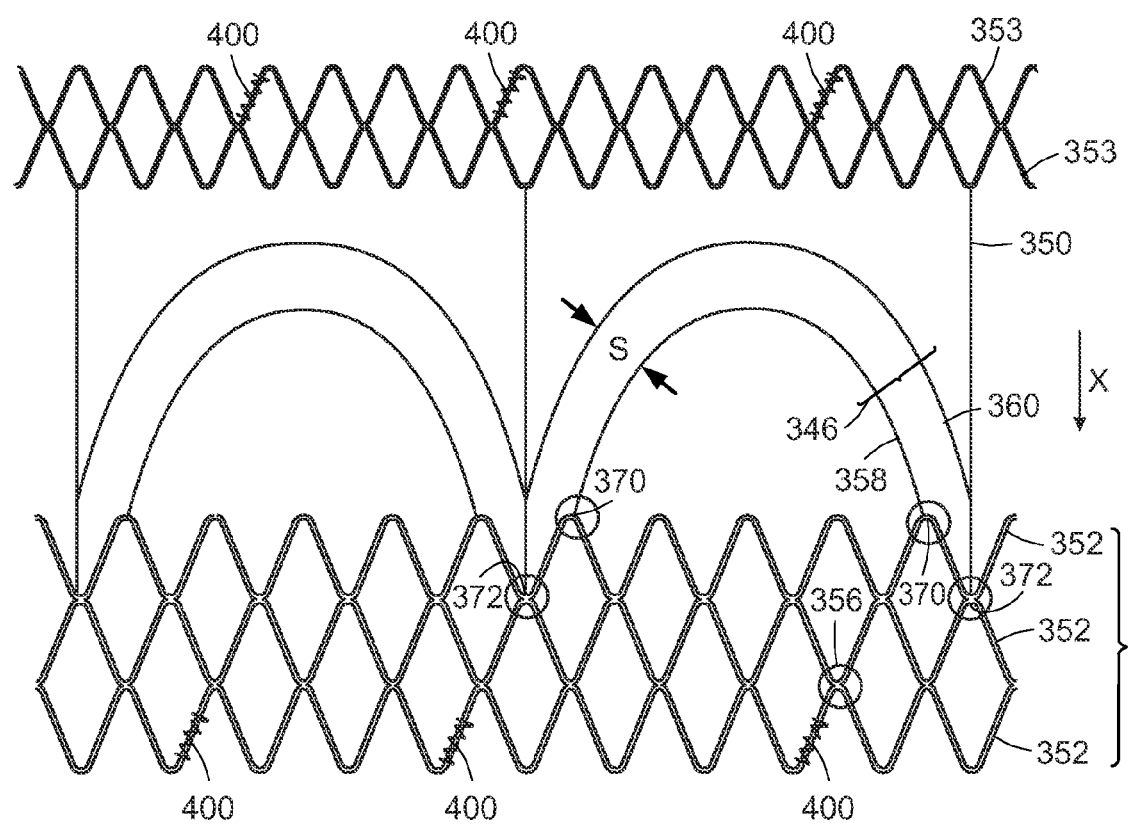
FIG. 8 is an opened view of a portion of another embodiment of a valve frame (without leaflets) according to the present teachings.
Figure 15:
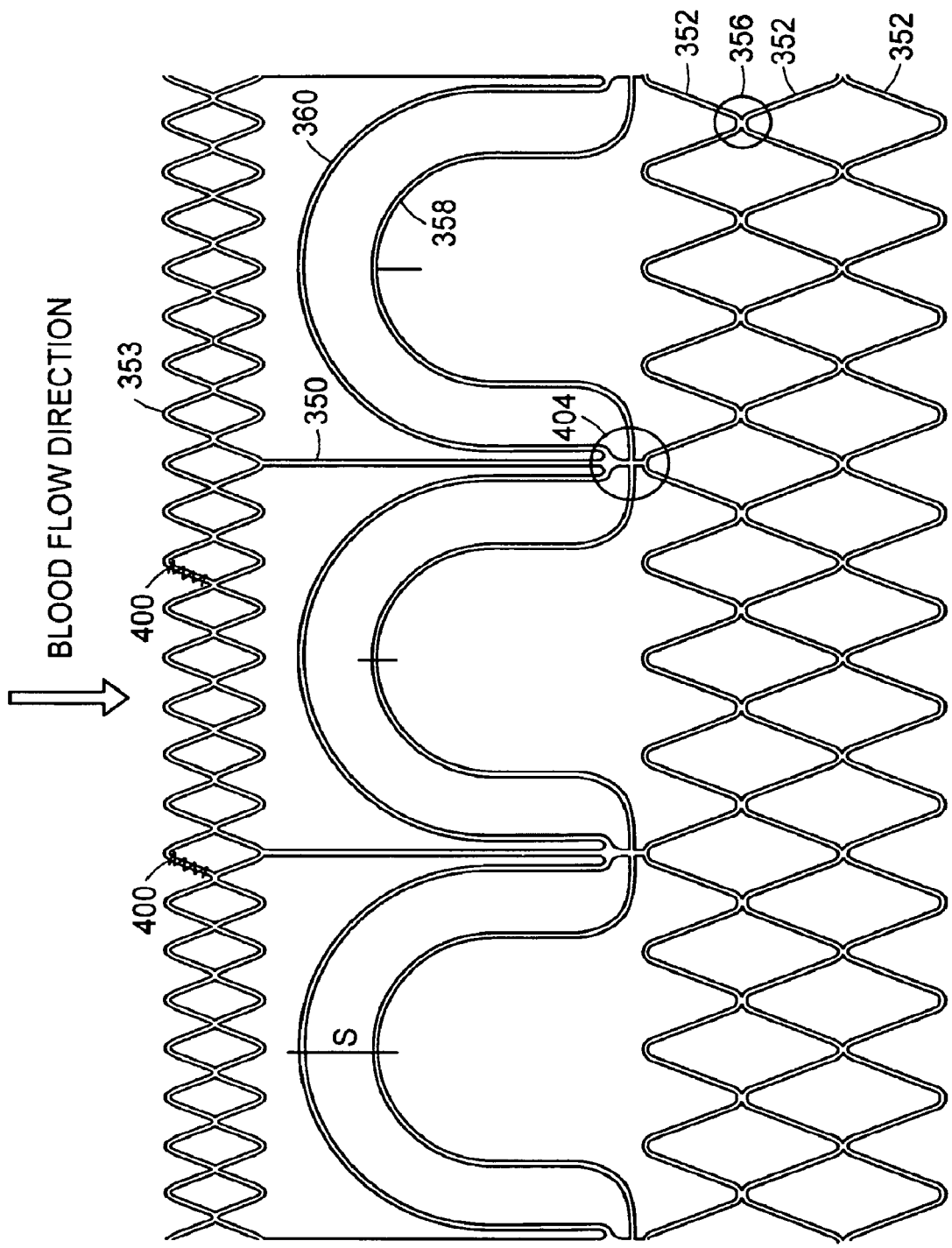
FIG. 15 is an opened view of a portion of another embodiment of a valve frame (without leaflets) of the invention.

At one end of the cylindrical body 341 of the valve frame 340 are three sets of valve attachment pairs 346 for attaching valve leaflets 390. Each valve attachment pair 346 can include an inner curved support structure 358 and an outer curved support structure 360. Each curved support structure 358, 360 can be attached either to a vertex 362, 364 (respectively as shown in FIG. 7) or to a trough 372 and vertex 370 (respectively as shown in FIG. 8). In some embodiments (as shown in FIGS. 8 and 15), the space S between the inner curved support structure 358 and the outer curved support structure 360 can be constant. The space S, for example, can be in the range of about 2-3 mm. The inner curved support structure 358 and the outer curved support structure 360, as well as the space S therebetween, can be substantially parabolic in shape (as shown in FIG. 8) or can resemble a pocket, i.e., a partial rectangle with rounded corners (as shown in FIG. 12).

By placing the attachment of the outer 360 and inner 358 curved support structures to the body 341 of the valve frame 340, at adjacent vertices 370 and troughs 372, the distance between the inner 358 and outer 360 curved support structures can be substantially assured. As a result, the movement of the valve leaflets 390 does not cause the curved support structures 358, 360 to touch, thereby preventing damage to the leaflets 390.

Figure 13:
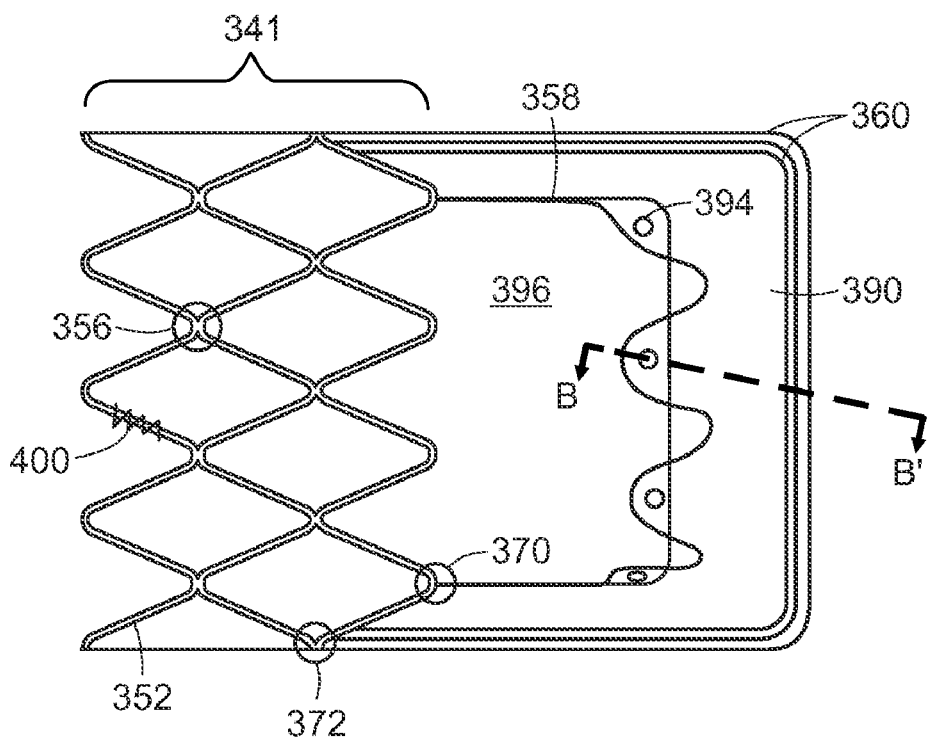
FIG. 13 is a plan view of the embodiment of the valve frame of FIG. 12 with leaflets attached.

In some embodiments, the inner curved support structure 358 and the outer curved support structure 360 can each include one piece of wire only (shown in FIG. 8). In other embodiments, the inner curved support structure 358 can have one piece of wire, while the outer curved support structure 360 can have two or more pieces of wire (shown in FIG. 12). It is preferred that the two or more pieces of wire of the outer curved support structure 360 are spaced as closely as possible but still permit passage of the chosen cover material 396 (shown in FIGS. 13 and 14). For example, the cover material can have a thickness of 0.4 mm to about 1.0 mm, and the space between the wires of the outer curved support structure can be within the range of about 0.5 mm to about 1.0 mm.

Figure 9:
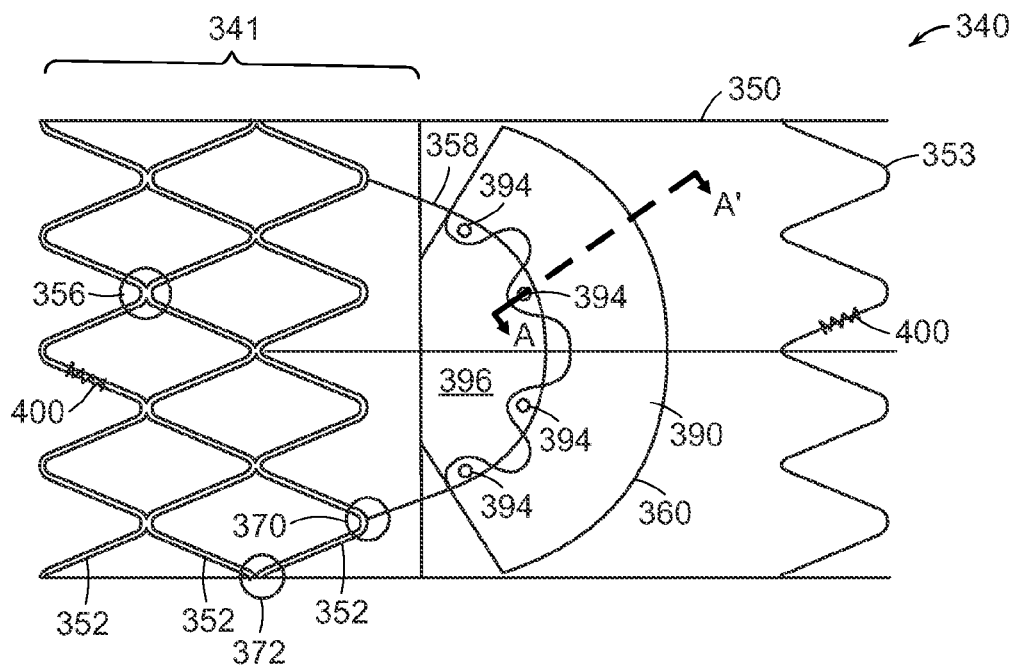
FIG. 9 is a plan view of the embodiment of the valve frame of FIG. 7 with leaflets attached.
Figure 10:
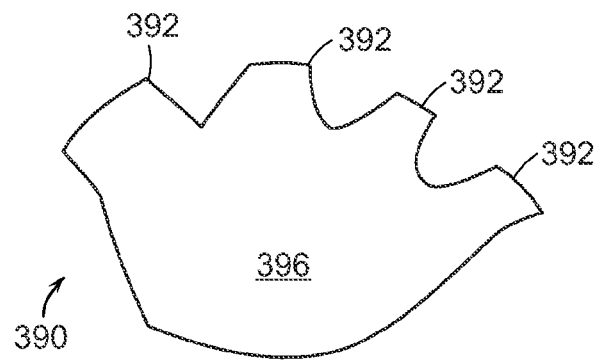
FIG. 10 is a plan view of an embodiment of a leaflet of a replacement heart valve.

More details of the leaflet 390 are shown in FIG. 10. With reference to FIGS. 9, 10, 11, 13 and 14, a leaflet 390 can attached to each valve attachment pair 346. Each leaflet 390 has a leaflet body 396 and a plurality of leaflet projections 392. When attached to the valve frame 340, the leaflet body 396 is located within the lumen of the valve frame 340.

Figure 11:
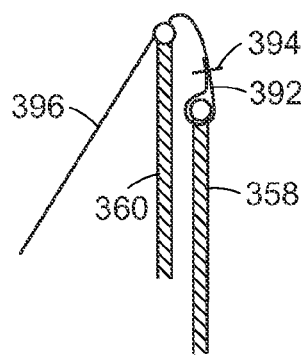
FIG. 11 is a cross-sectional view through line AA' of FIG. 9 showing the attachment of the leaflet to the inner curved support structure and the placement of the leaflet over the outer curved support structure.

Referring to FIG. 11, the leaflet 390 can be positioned such that the portion of the leaflet body 396 nearest the projections 392 is pulled over the outer curved support structure 360 and the leaflet projections 392 are curved over the inner curved support structure 358. Each leaflet projection 392 can be attached by sutures 394 to itself. This anchors the leaflet projections 392 to the inner curved support structure 358 and permits the leaflet body 396 to be secured and maintain its shape within the lumen of the valve frame 340. This configuration can prevent the sutures 394 from being exposed to blood passing through the valve and can provide free motion of the leaflet body without any contact to prosthetic materials thereby preventing damage to the leaflet.

Figure 14:
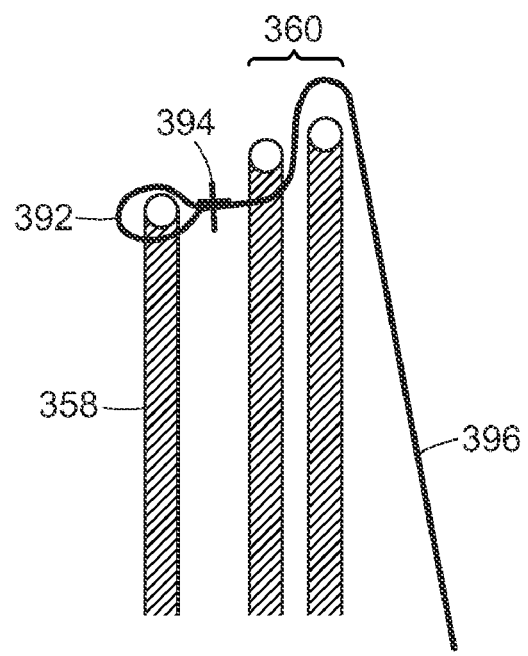
FIG. 14 is a cross-sectional view through BB' of FIG. 13 showing the attachment of the leaflet to the inner curved support structure and the placement of the leaflet over and between the outer curved support structure.

In the embodiment shown in FIG. 14, the two wires of the outer curved support structure 360 are placed very close to each other. Similar to the embodiment shown in FIG. 11, the leaflet 390 is positioned such that the portion of the leaflet body 396 nearest the projections 392 is pulled over the outermost wire of the outer curved support structure 360. Each of the leaflet projections 392 then passes through the space between the two wires of the outer curved support structure 360. Because the space between these two wires is designed to barely allow passage of the cover material 396, displacement of the leaflet between the docking station and the valve frame is minimized, in addition to the other advantages described in accordance with the embodiment shown in FIG. 11. Each of the leaflet projections 392 then wraps over the inner curved support structure 358 and is attached by sutures 394 to itself as in the other embodiment.

FIG. 15 depicts a similar valve frame but one in which the inner 358 and outer 360 curved support structures are attached to the same location 404 on vertices of wire 352 of the cylindrical body 352. Additionally, a plurality of standoffs 350 hold one or more exterior serpentine rings 353 at a distance away from the outer curved support structure 360 to provide extra support to the valve frame 340. At several locations on the exterior serpentine ring(s) 353 are located platinum markers 400. In some embodiments (shown) platinum wire is wrapped about the exterior serpentine ring(s) 353 in several locations. These locations then serve as radiopaque markers 400 to help position the valve frame 340 within the docking station 330. In other embodiments, the platinum markers are also positioned on the opposite end of the valve frame so that both ends of the valve frame 340 can be seen clearly under fluoroscopy as the valve frame 340 is positioned within the docking station 330. Each standoff 350 can be sufficiently long so that when the valve frame 340 is compressed to fit within a catheter, the leaflet 396 which is turned over the outer support structure 360 does not contact the exterior serpentine ring 353 thereby potentially causing damage to the leaflet 390. Similar platinum markers can be positioned on one or both ends of any of the valve frames described hereinabove, including the valve frames shown in FIGS. 8 and 12.

With reference to FIGS. 16A-16D, general method steps associated with the implantation of a transcatheter heart valve prosthesis according to the present teachings are described. By way of example, the method steps relate to implantation of the prosthesis in the aortic position; however, implantation of the prosthesis in other anatomical positions, for example, at the pulmonary valve position, is within the scope of the present teachings.

Figure 16A:
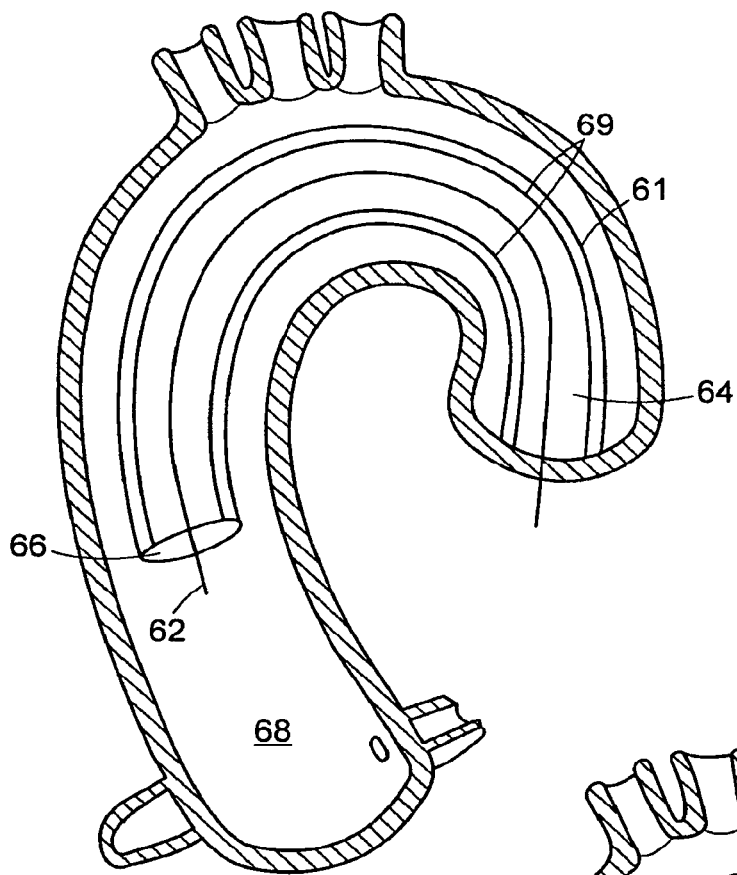
FIGS. 16A-16D illustrate an embodiment of implanting a heart valve prosthesis according to the present teachings.

Referring to FIG. 16A, an introducing catheter 61 is delivered via a femoral vessel by means of a guidewire 62 to the ascending aorta 68 at a position distal to the native aortic valve (away from the left ventricle). The introducing catheter 61 has an inner wall 69 that defines a lumen 64 through which the guidewire 62 is passed. The introducing catheter 61 has an opening 66 out of which the guidewire 62 is extended.

Figure 16B:
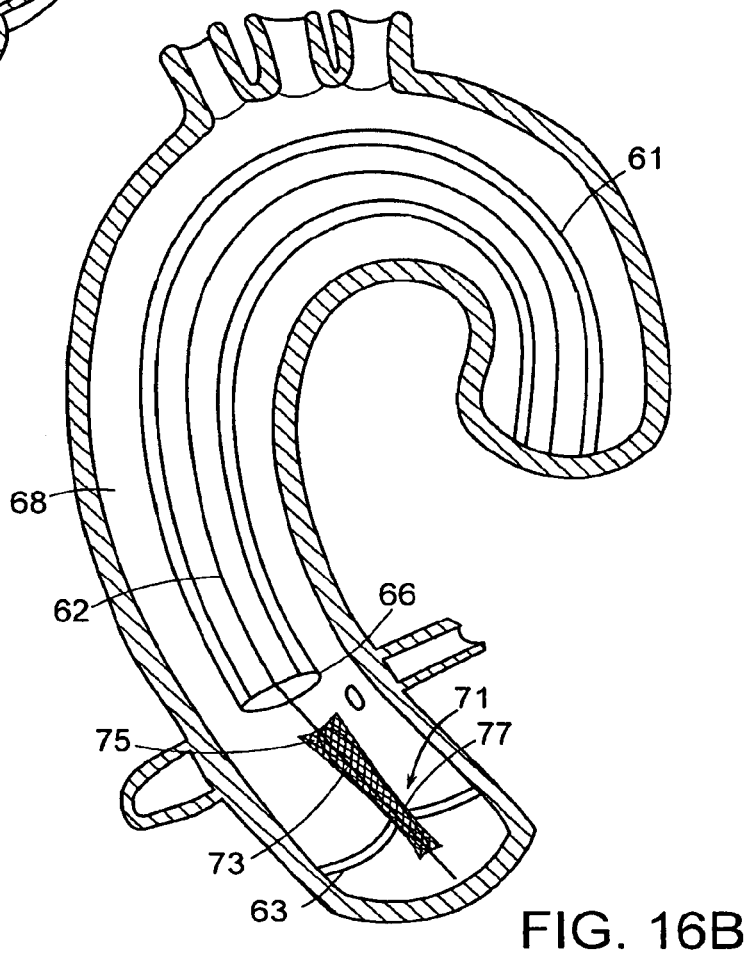

With reference also to FIG. 16B, a docking station/balloon combination 71 is inserted into the introducing catheter 61 and is guided to the ascending aorta 68 using the guidewire 62. The combination 71 is then deployed from the confines of the introducing catheter 61 and at least a portion of the docking station is positioned proximal to the native aortic valve 63. The docking station/balloon combination 71 can include a balloon 73 located within a lumen 75 of the docking station 77. In some embodiments, the docking station/balloon combination 71 can be positioned within the introducing catheter 61 prior to inserting the introducing catheter 61 into the anatomical lumen 65. In other embodiments, the docking station/balloon combination 71 can be inserted into the introducing catheter 61 after the opening 66 of the introducing catheter 61 has been located at the ascending aorta. As shown in FIG. 16B, the docking station/balloon combination is ready to be deployed in the same luminal space as the native aortic valve. The balloon of the deployed docking station/balloon combination is then inflated, thereby expanding the docking station to a predetermined configuration and size. The balloon is quickly deflated and withdrawn.

Figure 16C:
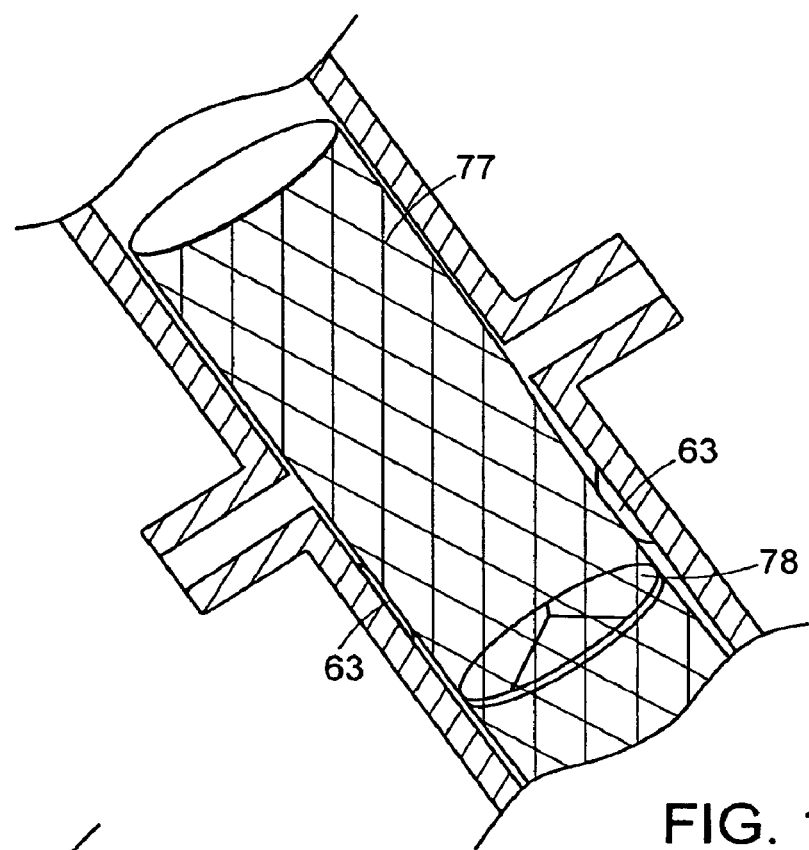

With reference to FIG. 16C, the deployed docking station 77 pushes the native aortic valve 63 against the wall of the aorta. As previously mentioned, such coverage and immobilization of the native heart valve typically will result in free regurgitation; however, due to the presence of the diaphragm 78 attached to the docking station, a controlled mechanism of blood flow is provided, thereby allowing the patient's heart to stabilize prior to the introduction of the more permanent replacement heart valve.

At this point, the medical practitioner, using fluoroscopy, can determine the diameter of the deployed docking station more precisely and select a valve frame of an optimal size. Once an appropriate valve frame is selected, it is compressed and inserted into the introducing catheter and the valve frame is guided to the catheter orifice and deployed into the lumen of the expanded docking station. In some embodiments, the valve frame can be deployed in or near the position at which the diaphragm is attached to the docking station.

Figure 16D:
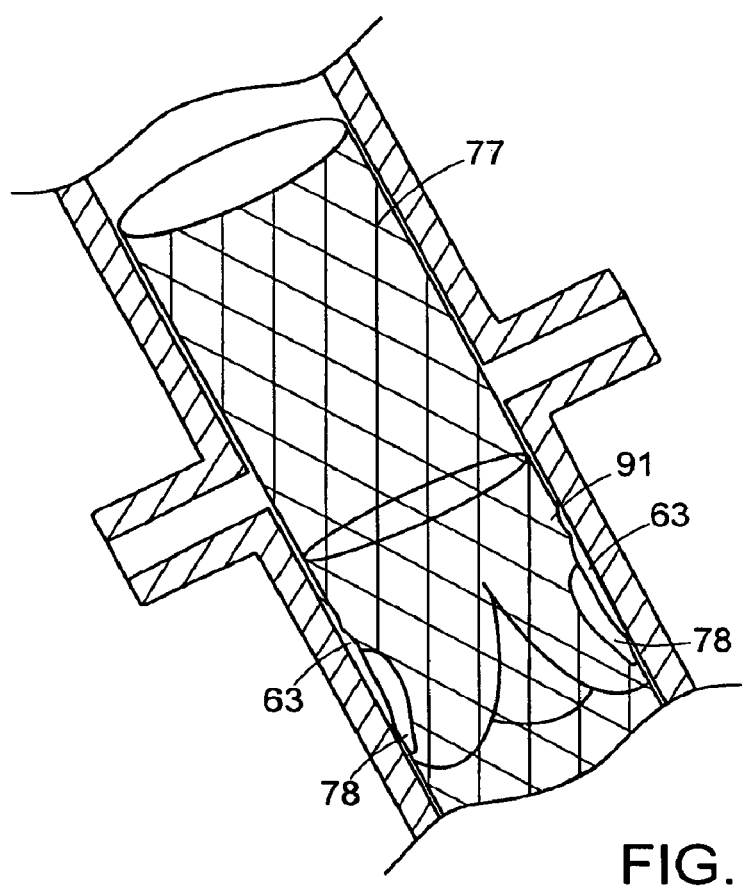

Referring to FIG. 16D, the valve frame 91 is deployed about the position at which the diaphragm 78 is attached within the lumen of the docking station 77. For example, the proximal portion (i.e., the portion having the valve members) of the valve frame can be positioned below where the diaphragm is attached to the docking station, while the distal portion of the valve frame can be positioned above where the diaphragm is attached. The diaphragm is pushed against the inner wall of the docking station and helps to seal any space that may exist between the docking station 77 and the valve frame 91. An additional benefit of the heart valve prosthesis of the present teachings therefore includes the provision of a sealing mechanism between the docking station and the valve frame, hence preventing any paravalvar leakage despite the fact that the valve frame 91 is adapted to expand and assume substantially the same size and shape as the lumen 75 of the expanded docking station 77 upon deployment. The introducing catheter can now be removed from the patient's body.

To further illustrate, the prosthesis of the present teachings can be implanted in the mitral position, for example, by generally following the steps described above. In particular, an introducing catheter and the prosthesis can be delivered through a femoral venous sheath, and the prosthesis can then be positioned in the left atrium and ventricle by making a hole in the atrial septum.

Figure 17A:
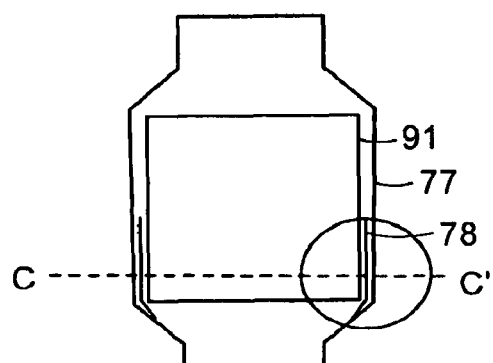
FIG. 17A is a schematic drawing showing the side view of an embodiment of a transcatheter heart valve prosthesis according to the present teachings.

FIG. 17A is a side cross-section view of a deployed docking station 77 with an attached diaphragm 78 within its lumen. A deployed replacement heart valve 91 (shown as a simplified block), interchangeably referred hereinbelow as a permanent valve, is positioned just above the attachment point of the diaphragm. As shown, the leaflets of the diaphragm are pushed against the inner wall of the docking station, similar to the way the deployed docking station pushes the cusps of the aortic valve against the wall of the aorta in FIG. 16C.

Figure 17B:
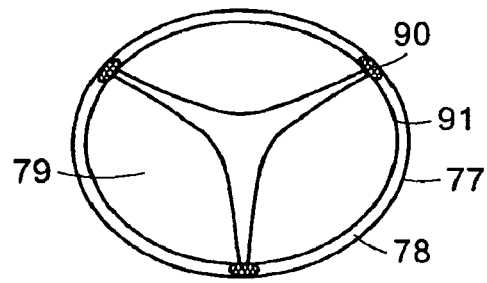
FIG. 17B is a cross-sectional view of the transcatheter heart valve prosthesis of FIG. 17A along the line C-C'.
Figure 17C:
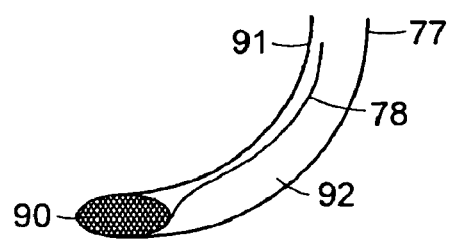
FIG. 17C is an expanded view of the circled portion of FIG. 17A.

FIG. 17B shows a cross-sectional view of the heart valve prosthesis of FIG. 17A along the line C-C'. The permanent valve 91 can include a plurality of leaflets 79 and one or more struts 90 that are similar to the standoffs 350 of valve frame 340 (FIGS. 7-9). As shown, the diaphragm is compressed between the docking station 77 and the permanent valve 91. FIG. 17C is an expanded view of the circled portion of FIG. 17A, which shows the potential space 92 between the docking station 77 and the permanent valve 91 more clearly.

Figure 18A:
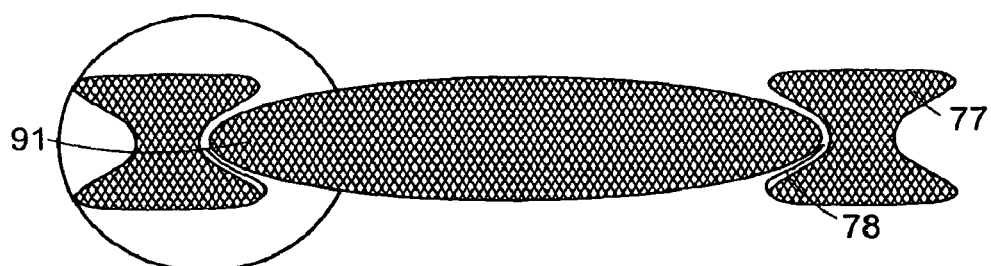
FIG. 18A is a schematic drawing showing the side view of an embodiment of a transcatheter heart valve prosthesis according to the present teachings.
Figure 18B:
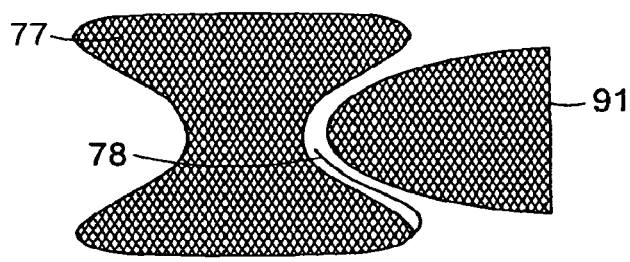
FIG. 18B is an expanded view of the circled portion of FIG. 18A.

FIG. 18A is a side cross-sectional view of another embodiment of a deployed docking station 77 with an attached diaphragm 78 within its lumen. A deployed replacement heart valve 91 (shown without detail for simplification) is positioned within the narrower intermediate portion of the docking station to allow stable anchoring. Again, the leaflets of the diaphragm are pushed against the inner wall of the docking station and can be compressed between the potential space between the docking station and the replacement heart valve to help prevent or reduce paravalvar leakage (FIG. 18B).

FIGS. 19A-C show how the diaphragm can be compressed by the deployed permanent valve, thereby being rendered non-functional and non-obstructive. In some embodiments and referring to FIG. 19A, the diaphragm 78 can be compressed by the struts 90 or standoffs of the permanent valve 91. In other embodiments and referring to FIGS. 19B and 19C, the diaphragm 78 can be compressed by one or more cylindrical portions of the permanent valve 90, for example, the substantially cylindrical body portion 341 and the exterior serpentine wire ring 353 of the valve frame 340 (FIG. 7). As shown in FIGS. 19A-C, potential space 92 can be found between the leaflets of the permanent valve, between the docking station and the permanent valve, and between the docking station and the native valve (not shown). The diaphragm pressed against the inner wall of the docking station by the deployed permanent valve can serve a secondary function of preventing paravalvar leakage due to such potential space, particularly when the diaphragm is composed of a bio-absorbent material or a material that is otherwise impermeable to blood as described in certain embodiments above. for example, by expanding to fill up the space.

Variations, modifications, and other implementations of what is described herein will occur to those of ordinary skill in the art without departing from the spirit and the essential characteristics of the present teachings. Accordingly, the scope of the invention is to be defined not by the preceding illustrative description but instead by the following claims, and all changes that come within the meaning and range of equivalency of the claims are intended to be embraced therein.

What is claimed is:

1. A heart valve prosthesis comprising a docking station and a replacement heart valve, wherein:
   the docking station comprises
      a wire frame defining a lumen, and
      a diaphragm positioned within the lumen and attached to the wire frame of the docking station prior to deployment, wherein the diaphragm is thinner and has less structural integrity than the replacement heart valve, and is adapted to have an open position and a closed position, and the replacement heart valve comprises a valve frame for positioning within the lumen of the docking station, wherein the valve frame of the replacement heart valve comprises a substantially cylindrical body defining a lumen and a plurality of valve members attached to the substantially cylindrical body, and each of the valve members comprises one or more curved wires and a leaflet.

2. The heart valve prosthesis of claim 1, wherein the docking station is self-expandable.

3. The heart valve prosthesis of claim 1, wherein the docking station is balloon-expandable.

4. The heart valve prosthesis of claim 1, wherein the wire frame of the docking station comprises one or more openings.

5. The heart valve prosthesis of claim 1 comprising a radiopaque marker on the wire frame of the docking station.

6. The heart valve prosthesis of claim 1, wherein the diaphragm comprises a biocompatible membrane.

7. The heart valve prosthesis of claim 1, wherein the diaphragm comprises one or more slits.

8. The heart valve prosthesis of claim 1, wherein the diaphragm comprises a plurality of leaflets.

9. The heart valve prosthesis of claim 8, wherein the leaflets of the diaphragm are supported by one or more wires.

10. The heart valve prosthesis of claim 1, wherein the diaphragm comprises one or more perforations.

11. The heart valve prosthesis of claim 1, wherein the diaphragm is attached to the wire frame of the docking station by sutures.

12. The heart valve prosthesis of claim 1, wherein the diaphragm is attached to the wire frame of the docking station by adhesives.

13. The heart valve prosthesis of claim 1, wherein the wire frame of the docking station comprises a cylindrical portion and a bulbous portion, the diaphragm being attached to the bulbous portion of the wire frame.

14. The heart valve prosthesis of claim 1, wherein the one or more curved wires of each of the valve members of the replacement heart valve comprises an inner curved wire support structure and an outer curved wire support structure.

15. The heart valve prosthesis of claim 14, wherein the leaflet of each of the valve members of the replacement heart valve comprises a leaflet body and one or more leaflet projections.

16. The heart valve prosthesis of claim 15, wherein the one or more leaflet projections are attached to a respective inner curved support structure and the leaflet body extends over a respective outer curved support structure, so as to position the leaflet body within the lumen of the valve frame of the replacement heart valve.

17. A method of delivering the heart valve prosthesis of claim 1 to an anatomical site, the method comprising the steps of:
introducing the docking station into a heart through a catheter
deploying the docking station;
introducing the replacement heart valve into the lumen of the docking station through a catheter; and
deploying the replacement heart valve within the lumen of the docking station so that the diaphragm is forced into the open position and leaflets of the diaphragm are pressed between the wire frame of the docking station and the valve members of the replacement heart valve.

18. The method of claim 17 further comprising determining a diameter of the deployed docking station using fluoroscopy.

19. The method of claim 18, wherein the replacement heart valve has a diameter that approximates the diameter of the deployed docking station.

* * * * *